(12) United States Patent
Seegert et al.

(10) Patent No.: US 8,206,948 B2
(45) Date of Patent: Jun. 26, 2012

(54) OPTIMIZED NUCLEOTIDE SEQUENCES ENCODING SGP130

(75) Inventors: Dirk Seegert, Altenholz (DE); Georg Wätzig, Kiel (DE); Nikolaus Rahaus, Kiel (DE); Jessica Daecke, Weinheim (DE); Stefan Rose-John, Schellhorn (DE)

(73) Assignee: Conaris Research Institute AG, Kiel (DE)

( * ) Notice: Subject to any disclaimer, the term of this patent is extended or adjusted under 35 U.S.C. 154(b) by 450 days.

(21) Appl. No.: 11/660,461

(22) PCT Filed: Aug. 26, 2005

(86) PCT No.: PCT/EP2005/009247
§ 371 (c)(1),
(2), (4) Date: Nov. 16, 2007

(87) PCT Pub. No.: WO2006/021453
PCT Pub. Date: Mar. 2, 2006

(65) Prior Publication Data
US 2008/0199906 A1 Aug. 21, 2008

(30) Foreign Application Priority Data
Aug. 27, 2004 (EP) .................................. 04020455

(51) Int. Cl.
*C12N 15/09* (2006.01)
*C12N 15/11* (2006.01)
*C12N 5/07* (2010.01)
*C07H 21/04* (2006.01)
*C12N 15/24* (2006.01)
*C12P 21/04* (2006.01)

(52) U.S. Cl. .................. 435/69.1; 435/252.3; 435/320.1; 435/325; 435/358; 435/369; 536/23.5; 530/351

(58) Field of Classification Search .................. None
See application file for complete search history.

(56) References Cited

U.S. PATENT DOCUMENTS
6,472,179 B2 * 10/2002 Stahl et al. .................. 435/69.7
2002/0012962 A1 1/2002 Stahl et al.

FOREIGN PATENT DOCUMENTS
| EP | 1148065 A1 | 10/2001 |
| WO | WO 95/33059 A2 | 12/1995 |
| WO | WO 95/33059 A3 | 1/1996 |
| WO | WO 2004/113383 A2 | 12/2004 |
| WO | WO 2004/113383 A3 | 12/2004 |

OTHER PUBLICATIONS

Tanaka et al., J. Clin. Invest. 106:137-144, 2000.*
Lazar et al, Mol. Cell. Biol. 1988, vol. 8, pp. 1247-1252.*
Wells, 1990, Biochemistry 29:8509-8517.*
Ancey, et al. A fusion protein of the gp130 and interleukin-6Ralpha ligand-binding domains acts as a potent interleukin-6 inhibitor. J Biol Chem. May 9, 2003;278(19):16968-16972.
Chow, et al. In vitro reconstitution of recognition and activation complexes between interleukin-6 and gp130. Biochemistry. Jun. 26, 2001;40(25):7593-7603.
Fuglsang, et al. Codon optimizer: a freeware tool for codon optimization. Protein Expr Purif. Oct. 2003;31(2):247-249.
Horsten, et al. The membrane distal half of gp130 is responsible for the formation of a ternary complex with IL-6 and the IL-6 receptor. FEBS Lett. Feb. 20,1995;360(1):4346.
Kallen, K. J. The role of trans signalling via the agonistic soluble IL-6 receptor in human diseases. Biochim Biophys Acta. Nov. 11, 2002;1592(3):323-343.
Wada, et al. Codon usage tabulated from the GenBank genetic sequence data. Nucleic Acids Res. Apr. 25, 1990; 18(Suppl): 2367-2411.
Colbere-Garapin, et al. A new dominant hybrid selective marker for higher eukaryotic cells. J Mol Biol. Jul. 25, 1981;150(1):1-14.
Gao, et al. UpGene: Application of a web-based DNA codon optimization algorithm. Biotechnol Prog. Mar.-Apr. 2004;20(2):443-8.
Hartman, et al. Two dominant-acting selectable markers for gene transfer studies in mammalian cells. Proc Natl Acad Sci U S A. Nov. 1988;85(21):8047-51.
Java Codon Adaption Tool. JCat, available at http://www.prodoric.de/JCat/, 2008.
Jostock, et al. Soluble gb130 is the natural inhibitor of soluble interleukin-6 receptor transsignaling responses. Eur. J. biochem. 2001; 268:160-7 (figure 1; upper panel).
Logan, et al. Adenovirus tripartite leader sequence enhances translation of mRNAs late after infection. Proc Natl Acad Sci U S A. Jun. 1984;81(12):3655-9.
Lowy, et al. Isolation of transforming DNA: cloning the hamster aprt gene. Cell. Dec. 1980;22(3):817-23.
Nakamura, et al. Codon usage tabulated from the international DNA sequence databases. Nucleic Acids Research. 1996, 24:214-5.
Rhodes, et al. Identification of MRF4: a new member of the muscle regulatory factor gene family. Genes Dev. Dec. 1989;3(12B):2050-61.
Sambrook, J. Molecular Cloning: A Laboratory Manual. Cold Spring Harbor Laboratory Press, Cold Spring Harbor, NY (1989).
Scharf, et al. Heat stress promoters and transcription factors. Results Probl Cell Differ. 1994;20:125-62. Wigler, et al. Transfer of purified herpes virus thymidine kinase gene to cultured mouse cells. Cell. May 1977;11(1):223-32.
Wigler, et al. Transformation of mammalian cells with an amplifiable dominant-acting gene. Proc Natl Acad Sci U S A. Jun. 1980;77(6):3567-70.

* cited by examiner

*Primary Examiner* — Bridget E Bunner
*Assistant Examiner* — Fozia Hamud
(74) *Attorney, Agent, or Firm* — Wilson, Sonsini, Goodrich & Rosati

(57) ABSTRACT

Described are codon optimized sgp130 encoding nucleic acid molecules as well as a method for the highly efficient recombinant production of sgp130 in mammalian cells or bacteria using a nucleic acid molecule of the invention.

9 Claims, 19 Drawing Sheets

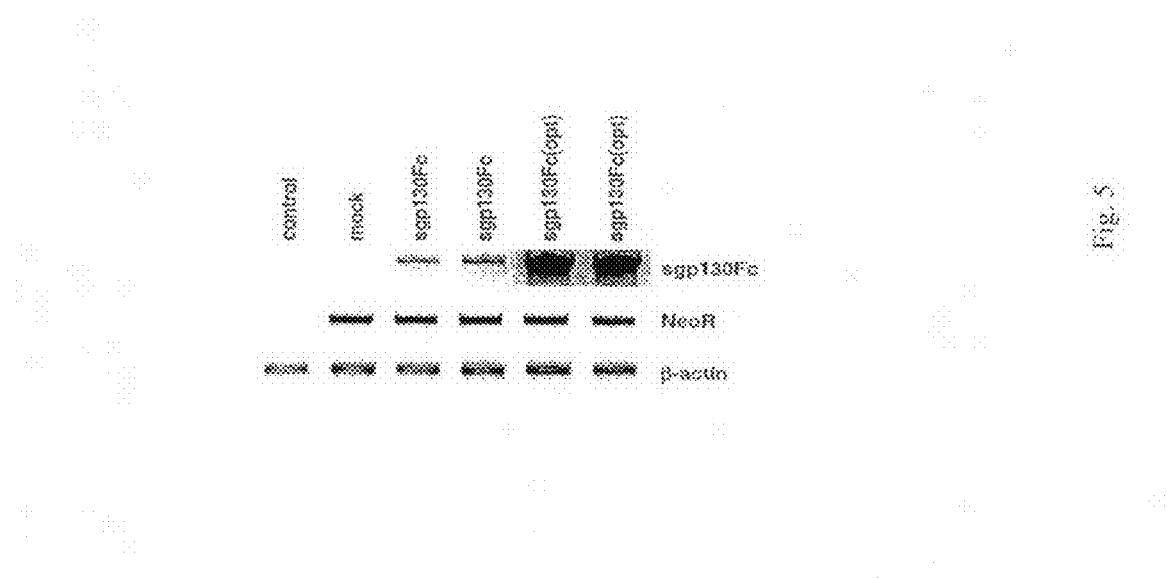

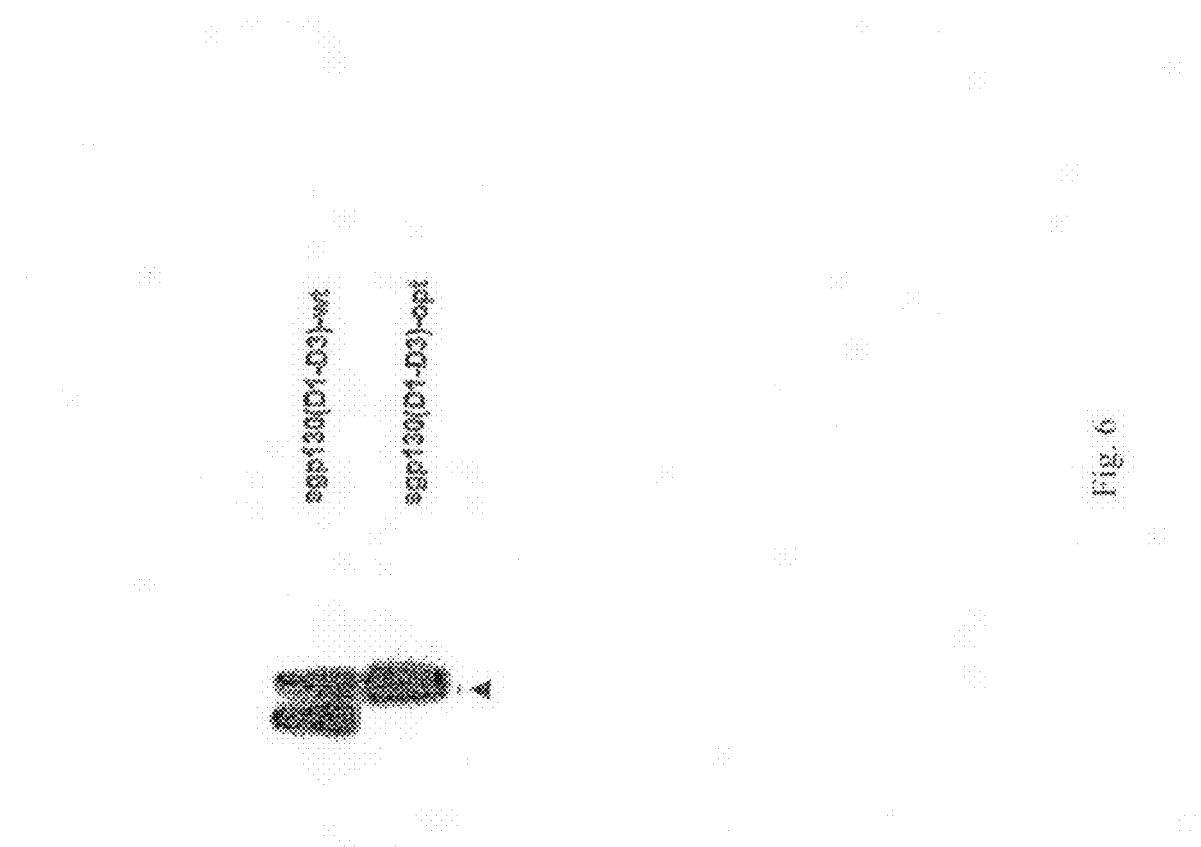

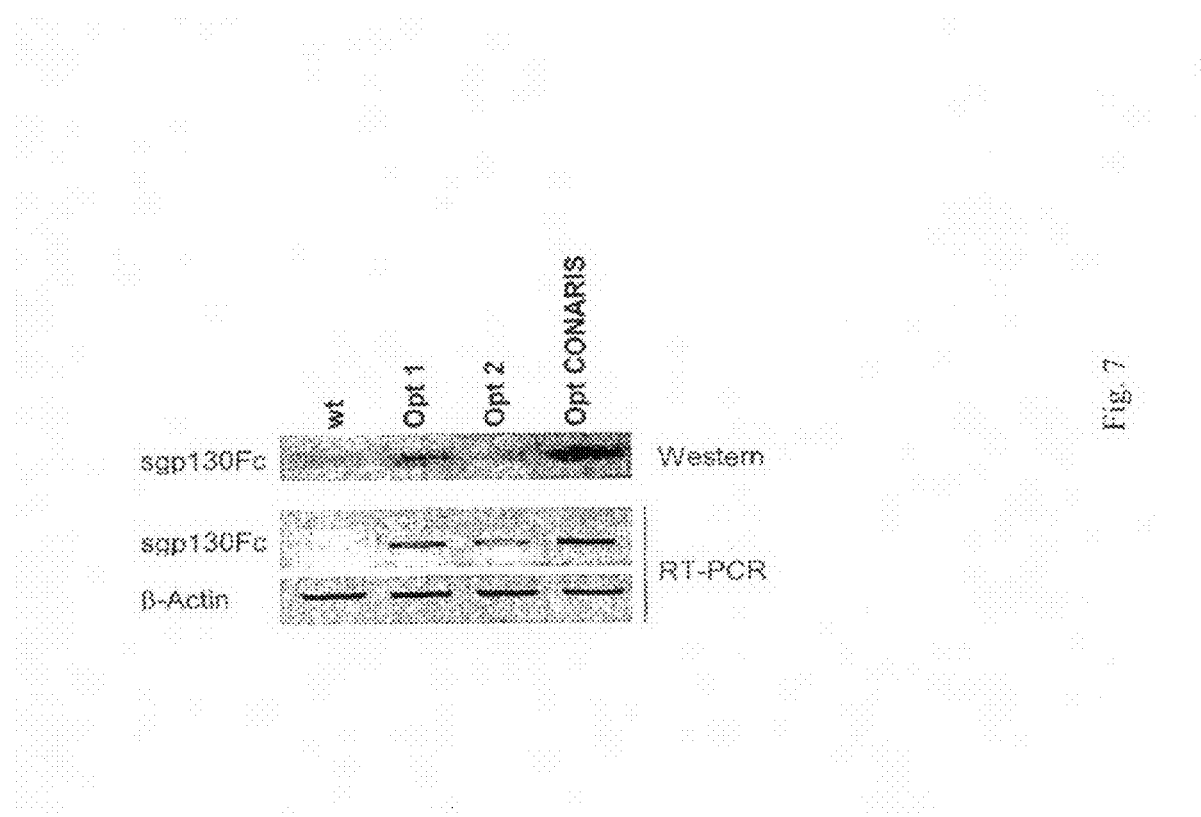

|            | wt  | opt_Con | opt_JCat | opt_UpGene |
|------------|-----|---------|----------|------------|
| wt         | -   | 561     | 626      | 588        |
| opt_Con    | 561 | -       | 383      | 405        |
| opt_JCat   | 626 | 383     | -        | 404        |
| opt_UpGene | 588 | 405     | 404      | -          |

Fig. 9

SEQUENCE LISTING

```
<160> NUMBER OF SEQ ID NOS: 17

<210> SEQ ID NO 1
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Leu Thr Leu Gln Thr Trp Val Val Gln Ala Leu Phe Ile Phe Leu
 1               5                   10                  15

Thr Thr Glu Ser Thr Gly
            20
```

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atgaggtgtg agtgggatgg                                              20

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
accttgcact tgtactcctt gc                                           22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gatgcctgct tgccgaatat c                                            21

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgccaagctc ttcagcaata tc                                           22

<210> SEQ ID NO 6
<211> LENGTH: 918
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(915)

<400> SEQUENCE: 6 atg gaa ctg ctg gac ccg tgc ggt tat atc agc ccg gaa agc cca gtt      48
Met Glu Leu Leu Asp Pro Cys Gly Tyr Ile Ser Pro Glu Ser Pro Val
 1               5                  10                  15 gtt caa ctg cat agc aat ttc acc gcg gtt tgt gtg ctg aaa gag aag      96
Val Gln Leu His Ser Asn Phe Thr Ala Val Cys Val Leu Lys Glu Lys
             20                  25                  30 tgt atg gat tat ttc cac gtc aac gcg aac tac att gtg tgg aaa acc     144
Cys Met Asp Tyr Phe His Val Asn Ala Asn Tyr Ile Val Trp Lys Thr
         35                  40                  45 aac cat ttc acc atc ccg aaa gaa cag tat acc atc att aac cgt acc     192

```
Asn His Phe Thr Ile Pro Lys Glu Gln Tyr Thr Ile Ile Asn Arg Thr
    50              55                  60 gcg agc agc gtt acc ttt acc gat atc gcg agc ctg aac att caa ctg      240
Ala Ser Ser Val Thr Phe Thr Asp Ile Ala Ser Leu Asn Ile Gln Leu
65              70                  75                  80 acc tgc aac att ctg acc ttc ggt caa ctg gaa cag aat gtt tat ggc      288
Thr Cys Asn Ile Leu Thr Phe Gly Gln Leu Glu Gln Asn Val Tyr Gly
                85                  90                  95 atc acc atc att agc ggc ctg ccg ccg gaa aaa ccg aaa aat ctg agc      336
Ile Thr Ile Ile Ser Gly Leu Pro Pro Glu Lys Pro Lys Asn Leu Ser
            100                 105                 110 tgc att gtg aac gaa ggc aaa aaa atg cgc tgc gaa tgg gat ggt ggt      384
Cys Ile Val Asn Glu Gly Lys Lys Met Arg Cys Glu Trp Asp Gly Gly
        115                 120                 125 cgc gaa acc cac ctg gaa acc aac ttc acc ctg aaa agc gaa tgg gcg      432
Arg Glu Thr His Leu Glu Thr Asn Phe Thr Leu Lys Ser Glu Trp Ala
    130                 135                 140 acc cac aaa ttt gcg gat tgc aaa gcg aaa cgc gat acc ccg acc tct      480
Thr His Lys Phe Ala Asp Cys Lys Ala Lys Arg Asp Thr Pro Thr Ser
145                 150                 155                 160 tgc acc gtt gat tac agc acc gtg tac ttc gtg aac att gaa gtg tgg      528
Cys Thr Val Asp Tyr Ser Thr Val Tyr Phe Val Asn Ile Glu Val Trp
                165                 170                 175 gtg gaa gcg gaa aac gcc ctg ggt aaa gtc acc agc gat cat atc aac      576
Val Glu Ala Glu Asn Ala Leu Gly Lys Val Thr Ser Asp His Ile Asn
            180                 185                 190 ttt gat ccg gtg tac aaa gtg aaa ccg aat ccg ccg cat aat ctg agc      624
Phe Asp Pro Val Tyr Lys Val Lys Pro Asn Pro Pro His Asn Leu Ser
        195                 200                 205 gtg atc aac agc gaa gaa ctg agc agc atc ctg aaa ctg acc tgg acc      672
Val Ile Asn Ser Glu Glu Leu Ser Ser Ile Leu Lys Leu Thr Trp Thr
    210                 215                 220 aac ccg agc att aag agc gtt atc atc ctg aaa tac aac att cag tat      720
Asn Pro Ser Ile Lys Ser Val Ile Ile Leu Lys Tyr Asn Ile Gln Tyr
225                 230                 235                 240 cgc acc aaa gat gcc agc acc tgg agc cag att ccg ccg gaa gat acc      768
Arg Thr Lys Asp Ala Ser Thr Trp Ser Gln Ile Pro Pro Glu Asp Thr
                245                 250                 255 gcg agc acc cgt agc agc ttc acc gtt cag gat ctg aaa ccg ttt acc      816
Ala Ser Thr Arg Ser Ser Phe Thr Val Gln Asp Leu Lys Pro Phe Thr
            260                 265                 270 gaa tat gtg ttt cgc att cgc tgt atg aaa gaa gat ggt aaa ggc tac      864
Glu Tyr Val Phe Arg Ile Arg Cys Met Lys Glu Asp Gly Lys Gly Tyr
        275                 280                 285 tgg agc gat tgg agc gaa gaa gcg agc ggt atc acc tat gaa gat cgt      912
Trp Ser Asp Trp Ser Glu Glu Ala Ser Gly Ile Thr Tyr Glu Asp Arg
    290                 295                 300 ccg tga                                                               918
Pro
305

<210> SEQ ID NO 7
<211> LENGTH: 918
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(915)

<400> SEQUENCE: 7
```

```
atg gaa ctt cta gat cca tgt ggt tat atc agt cct gaa tct cca gtt          48
Met Glu Leu Leu Asp Pro Cys Gly Tyr Ile Ser Pro Glu Ser Pro Val
 1               5                  10                 15 gta caa ctt cat tct aat ttc act gca gtt tgt gtg cta aag gaa aaa          96
Val Gln Leu His Ser Asn Phe Thr Ala Val Cys Val Leu Lys Glu Lys
             20                  25                 30 tgt atg gat tat ttt cat gta aat gct aat tac att gtc tgg aaa aca        144
Cys Met Asp Tyr Phe His Val Asn Ala Asn Tyr Ile Val Trp Lys Thr
         35                  40                 45 aac cat ttt act att cct aag gag caa tat act atc ata aac aga aca        192
Asn His Phe Thr Ile Pro Lys Glu Gln Tyr Thr Ile Ile Asn Arg Thr
     50                  55                 60 gca tcc agt gtc acc ttt aca gat ata gct tca tta aat att cag ctc        240
Ala Ser Ser Val Thr Phe Thr Asp Ile Ala Ser Leu Asn Ile Gln Leu
 65              70                  75                 80 act tgc aac att ctt aca ttc gga cag ctt gaa cag aat gtt tat gga        288
Thr Cys Asn Ile Leu Thr Phe Gly Gln Leu Glu Gln Asn Val Tyr Gly
             85                  90                 95 atc aca ata att tcg ggc ttg cct cca gaa aaa cct aaa aat ttg agt        336
Ile Thr Ile Ile Ser Gly Leu Pro Pro Glu Lys Pro Lys Asn Leu Ser
         100                 105                110 tgc att gtg aac gag ggg aag aaa atg agg tgt gag tgg gat ggt gga        384
Cys Ile Val Asn Glu Gly Lys Lys Met Arg Cys Glu Trp Asp Gly Gly
     115                 120                125 agg gaa aca cac ttg gag aca aac ttc act tta aaa tct gaa tgg gca        432
Arg Glu Thr His Leu Glu Thr Asn Phe Thr Leu Lys Ser Glu Trp Ala
 130                 135                140 aca cac aag ttt gct gat tgc aaa gca aaa cgt gac acc ccc acc tca        480
Thr His Lys Phe Ala Asp Cys Lys Ala Lys Arg Asp Thr Pro Thr Ser
145                 150                 155                160 tgc act gtt gat tat tct act gtg tat ttt gtc aac att gaa gtc tgg        528
Cys Thr Val Asp Tyr Ser Thr Val Tyr Phe Val Asn Ile Glu Val Trp
             165                 170                175 gta gaa gca gag aat gcc ctt ggg aag gtt aca tca gat cat atc aat        576
Val Glu Ala Glu Asn Ala Leu Gly Lys Val Thr Ser Asp His Ile Asn
         180                 185                190 ttt gat cct gta tat aaa gtg aag ccc aat ccg cca cat aat tta tca        624
Phe Asp Pro Val Tyr Lys Val Lys Pro Asn Pro Pro His Asn Leu Ser
     195                 200                205 gtg atc aac tca gag gaa ctg tct agt atc tta aaa ttg aca tgg acc        672
Val Ile Asn Ser Glu Glu Leu Ser Ser Ile Leu Lys Leu Thr Trp Thr
 210                 215                220 aac cca agt att aag agt gtt ata ata cta aaa tat aac att caa tat        720
Asn Pro Ser Ile Lys Ser Val Ile Ile Leu Lys Tyr Asn Ile Gln Tyr
225                 230                 235                240 agg acc aaa gat gcc tca act tgg agc cag att cct cct gaa gac aca        768
Arg Thr Lys Asp Ala Ser Thr Trp Ser Gln Ile Pro Pro Glu Asp Thr
             245                 250                255 gca tcc acc cga tct tca ttc act gtc caa gac ctt aaa cct ttt aca        816
Ala Ser Thr Arg Ser Ser Phe Thr Val Gln Asp Leu Lys Pro Phe Thr
         260                 265                270 gaa tat gtg ttt agg att cgc tgt atg aag gaa gat ggt aag gga tac        864
Glu Tyr Val Phe Arg Ile Arg Cys Met Lys Glu Asp Gly Lys Gly Tyr
     275                 280                285 tgg agt gac tgg agt gaa gaa gca agt ggg atc acc tat gaa gat aga        912
Trp Ser Asp Trp Ser Glu Glu Ala Ser Gly Ile Thr Tyr Glu Asp Arg
 290                 295                300 cca tga                                                                 918
Pro
305
```

<210> SEQ ID NO 8
<211> LENGTH: 305
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 8

```
Met Glu Leu Leu Asp Pro Cys Gly Tyr Ile Ser Pro Glu Ser Pro Val
  1               5                  10                  15

Val Gln Leu His Ser Asn Phe Thr Ala Val Cys Val Leu Lys Glu Lys
             20                  25                  30

Cys Met Asp Tyr Phe His Val Asn Ala Asn Tyr Ile Val Trp Lys Thr
         35                  40                  45

Asn His Phe Thr Ile Pro Lys Glu Gln Tyr Thr Ile Asn Arg Thr
     50                  55                  60

Ala Ser Ser Val Thr Phe Thr Asp Ile Ala Ser Leu Asn Ile Gln Leu
 65                  70                  75                  80

Thr Cys Asn Ile Leu Thr Phe Gly Gln Leu Glu Gln Asn Val Tyr Gly
                 85                  90                  95

Ile Thr Ile Ile Ser Gly Leu Pro Pro Glu Lys Pro Lys Asn Leu Ser
            100                 105                 110

Cys Ile Val Asn Glu Gly Lys Lys Met Arg Cys Glu Trp Asp Gly Gly
            115                 120                 125

Arg Glu Thr His Leu Glu Thr Asn Phe Thr Leu Lys Ser Glu Trp Ala
        130                 135                 140

Thr His Lys Phe Ala Asp Cys Lys Ala Lys Arg Asp Thr Pro Thr Ser
145                 150                 155                 160

Cys Thr Val Asp Tyr Ser Thr Val Tyr Phe Val Asn Ile Glu Val Trp
                165                 170                 175

Val Glu Ala Glu Asn Ala Leu Gly Lys Val Thr Ser Asp His Ile Asn
            180                 185                 190

Phe Asp Pro Val Tyr Lys Val Lys Pro Asn Pro Pro His Asn Leu Ser
        195                 200                 205

Val Ile Asn Ser Glu Glu Leu Ser Ser Ile Leu Lys Leu Thr Trp Thr
    210                 215                 220

Asn Pro Ser Ile Lys Ser Val Ile Ile Leu Lys Tyr Asn Ile Gln Tyr
225                 230                 235                 240

Arg Thr Lys Asp Ala Ser Thr Trp Ser Gln Ile Pro Pro Glu Asp Thr
                245                 250                 255

Ala Ser Thr Arg Ser Ser Phe Thr Val Gln Asp Leu Lys Pro Phe Thr
            260                 265                 270

Glu Tyr Val Phe Arg Ile Arg Cys Met Lys Glu Asp Gly Lys Gly Tyr
        275                 280                 285

Trp Ser Asp Trp Ser Glu Glu Ala Ser Gly Ile Thr Tyr Glu Asp Arg
    290                 295                 300

Pro
305
```

<210> SEQ ID NO 9
<211> LENGTH: 305
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 9

```
Met Glu Leu Leu Asp Pro Cys Gly Tyr Ile Ser Pro Glu Ser Pro Val
 1               5                  10                  15

Val Gln Leu His Ser Asn Phe Thr Ala Val Cys Val Leu Lys Glu Lys
             20                  25                  30

Cys Met Asp Tyr Phe His Val Asn Ala Asn Tyr Ile Val Trp Lys Thr
         35                  40                  45

Asn His Phe Thr Ile Pro Lys Glu Gln Tyr Thr Ile Asn Arg Thr
     50                  55                  60

Ala Ser Ser Val Thr Phe Thr Asp Ile Ala Ser Leu Asn Ile Gln Leu
 65                  70                  75                  80

Thr Cys Asn Ile Leu Thr Phe Gly Gln Leu Glu Gln Asn Val Tyr Gly
                 85                  90                  95

Ile Thr Ile Ile Ser Gly Leu Pro Pro Glu Lys Pro Lys Asn Leu Ser
            100                 105                 110

Cys Ile Val Asn Glu Gly Lys Lys Met Arg Cys Glu Trp Asp Gly Gly
            115                 120                 125

Arg Glu Thr His Leu Glu Thr Asn Phe Thr Leu Lys Ser Glu Trp Ala
130                 135                 140

Thr His Lys Phe Ala Asp Cys Lys Ala Lys Arg Asp Thr Pro Thr Ser
145                 150                 155                 160

Cys Thr Val Asp Tyr Ser Thr Val Tyr Phe Val Asn Ile Glu Val Trp
                165                 170                 175

Val Glu Ala Glu Asn Ala Leu Gly Lys Val Thr Ser Asp His Ile Asn
            180                 185                 190

Phe Asp Pro Val Tyr Lys Val Lys Pro Asn Pro Pro His Asn Leu Ser
            195                 200                 205

Val Ile Asn Ser Glu Glu Leu Ser Ser Ile Leu Lys Leu Thr Trp Thr
            210                 215                 220

Asn Pro Ser Ile Lys Ser Val Ile Ile Leu Lys Tyr Asn Ile Gln Tyr
225                 230                 235                 240

Arg Thr Lys Asp Ala Ser Thr Trp Ser Gln Ile Pro Pro Glu Asp Thr
                245                 250                 255

Ala Ser Thr Arg Ser Ser Phe Thr Val Gln Asp Leu Lys Pro Phe Thr
            260                 265                 270

Glu Tyr Val Phe Arg Ile Arg Cys Met Lys Glu Asp Gly Lys Gly Tyr
            275                 280                 285

Trp Ser Asp Trp Ser Glu Glu Ala Ser Gly Ile Thr Tyr Glu Asp Arg
            290                 295                 300

Pro
305
```

<210> SEQ ID NO 10
<211> LENGTH: 2511
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(2508)

<400> SEQUENCE: 10

```
atg ttg acg ttg cag act tgg cta gtg caa gcc ttg ttt att ttc ctc      48
Met Leu Thr Leu Gln Thr Trp Leu Val Gln Ala Leu Phe Ile Phe Leu
 1               5                  10                  15
```

```
acc act gaa tct aca ggt gaa ctt cta gat cca tgt ggt tat atc agt      96
Thr Thr Glu Ser Thr Gly Glu Leu Leu Asp Pro Cys Gly Tyr Ile Ser
        20                  25                  30 cct gaa tct cca gtt gta caa ctt cat tct aat ttc act gca gtt tgt     144
Pro Glu Ser Pro Val Val Gln Leu His Ser Asn Phe Thr Ala Val Cys
    35                  40                  45 gtg cta aag gaa aaa tgt atg gat tat ttt cat gta aat gct aat tac     192
Val Leu Lys Glu Lys Cys Met Asp Tyr Phe His Val Asn Ala Asn Tyr
50                  55                  60 att gtc tgg aaa aca aac cat ttt act att cct aag gag caa tat act     240
Ile Val Trp Lys Thr Asn His Phe Thr Ile Pro Lys Glu Gln Tyr Thr
65                  70                  75                  80 atc ata aac aga aca gca tcc agt gtc acc ttt aca gat ata gct tca     288
Ile Ile Asn Arg Thr Ala Ser Ser Val Thr Phe Thr Asp Ile Ala Ser
                85                  90                  95 tta aat att cag ctc act tgc aac att ctt aca ttc gga cag ctt gaa     336
Leu Asn Ile Gln Leu Thr Cys Asn Ile Leu Thr Phe Gly Gln Leu Glu
                    100                 105                 110 cag aat gtt tat gga atc aca ata att tcg ggc ttg cct cca gaa aaa     384
Gln Asn Val Tyr Gly Ile Thr Ile Ile Ser Gly Leu Pro Pro Glu Lys
            115                 120                 125 cct aaa aat ttg agt tgc att gtg aac gag ggg aag aaa atg agg tgt     432
Pro Lys Asn Leu Ser Cys Ile Val Asn Glu Gly Lys Lys Met Arg Cys
130                 135                 140 gag tgg gat ggt gga agg gaa aca cac ttg gag aca aac ttc act tta     480
Glu Trp Asp Gly Gly Arg Glu Thr His Leu Glu Thr Asn Phe Thr Leu
145                 150                 155                 160 aaa tct gaa tgg gca aca cac aag ttt gct gat tgc aaa gca aaa cgt     528
Lys Ser Glu Trp Ala Thr His Lys Phe Ala Asp Cys Lys Ala Lys Arg
                165                 170                 175 gac acc ccc acc tca tgc act gtt gat tat tct act gtg tat ttt gtc     576
Asp Thr Pro Thr Ser Cys Thr Val Asp Tyr Ser Thr Val Tyr Phe Val
                    180                 185                 190 aac att gaa gtc tgg gta gaa gca gag aat gcc ctt ggg aag gtt aca     624
Asn Ile Glu Val Trp Val Glu Ala Glu Asn Ala Leu Gly Lys Val Thr
            195                 200                 205 tca gat cat atc aat ttt gat cct gta tat aaa gtg aag ccc aat ccg     672
Ser Asp His Ile Asn Phe Asp Pro Val Tyr Lys Val Lys Pro Asn Pro
210                 215                 220 cca cat aat tta tca gtg atc aac tca gag gaa ctg tct agt atc tta     720
Pro His Asn Leu Ser Val Ile Asn Ser Glu Glu Leu Ser Ser Ile Leu
225                 230                 235                 240 aaa ttg aca tgg acc aac cca agt att aag agt gtt ata ata cta aaa     768
Lys Leu Thr Trp Thr Asn Pro Ser Ile Lys Ser Val Ile Ile Leu Lys
                245                 250                 255 tat aac att caa tat agg acc aaa gat gcc tca act tgg agc cag att     816
Tyr Asn Ile Gln Tyr Arg Thr Lys Asp Ala Ser Thr Trp Ser Gln Ile
                    260                 265                 270 cct cct gaa gac aca gca tcc acc cga tct tca ttc act gtc caa gac     864
Pro Pro Glu Asp Thr Ala Ser Thr Arg Ser Ser Phe Thr Val Gln Asp
            275                 280                 285 ctt aaa cct ttt aca gaa tat gtg ttt agg att cgc tgt atg aag gaa     912
Leu Lys Pro Phe Thr Glu Tyr Val Phe Arg Ile Arg Cys Met Lys Glu
290                 295                 300 gat ggt aag gga tac tgg agt gac tgg agt gaa gaa gca agt ggg atc     960
Asp Gly Lys Gly Tyr Trp Ser Asp Trp Ser Glu Glu Ala Ser Gly Ile
305                 310                 315                 320 acc tat gaa gat aga cca tct aaa gca cca agt ttc tgg tat aaa ata    1008
Thr Tyr Glu Asp Arg Pro Ser Lys Ala Pro Ser Phe Trp Tyr Lys Ile
                325                 330                 335
```

```
gat cca tcc cat act caa ggc tac aga act gta caa ctc gtg tgg aag     1056
Asp Pro Ser His Thr Gln Gly Tyr Arg Thr Val Gln Leu Val Trp Lys
            340                 345                 350 aca ttg cct cct ttt gaa gcc aat gga aaa atc ttg gat tat gaa gtg     1104
Thr Leu Pro Pro Phe Glu Ala Asn Gly Lys Ile Leu Asp Tyr Glu Val
                355                 360                 365 act ctc aca aga tgg aaa tca cat tta caa aat tac aca gtt aat gcc     1152
Thr Leu Thr Arg Trp Lys Ser His Leu Gln Asn Tyr Thr Val Asn Ala
    370                 375                 380 aca aaa ctg aca gta aat ctc aca aat gat cgc tat cta gca acc cta     1200
Thr Lys Leu Thr Val Asn Leu Thr Asn Asp Arg Tyr Leu Ala Thr Leu
385                 390                 395                 400 aca gta aga aat ctt gtt ggc aaa tca gat gca gct gtt tta act atc     1248
Thr Val Arg Asn Leu Val Gly Lys Ser Asp Ala Ala Val Leu Thr Ile
                405                 410                 415 cct gcc tgt gac ttt caa gct act cac cct gta atg gat ctt aaa gca     1296
Pro Ala Cys Asp Phe Gln Ala Thr His Pro Val Met Asp Leu Lys Ala
            420                 425                 430 ttc ccc aaa gat aac atg ctt tgg gtg gaa tgg act act cca agg gaa     1344
Phe Pro Lys Asp Asn Met Leu Trp Val Glu Trp Thr Thr Pro Arg Glu
                435                 440                 445 tct gta aag aaa tat ata ctt gag tgg tgt gta tta tca gat aaa gca     1392
Ser Val Lys Lys Tyr Ile Leu Glu Trp Cys Val Leu Ser Asp Lys Ala
    450                 455                 460 ccc tgt atc aca gac tgg caa caa gaa gat ggt acc gtg cat cgc acc     1440
Pro Cys Ile Thr Asp Trp Gln Gln Glu Asp Gly Thr Val His Arg Thr
465                 470                 475                 480 tat tta aga ggg aac tta gca gag agc aaa tgc tat ttg ata aca gtt     1488
Tyr Leu Arg Gly Asn Leu Ala Glu Ser Lys Cys Tyr Leu Ile Thr Val
                485                 490                 495 act cca gta tat gct gat gga cca gga agc cct gaa tcc ata aag gca     1536
Thr Pro Val Tyr Ala Asp Gly Pro Gly Ser Pro Glu Ser Ile Lys Ala
            500                 505                 510 tac ctt aaa caa gct cca cct tcc aaa gga cct act gtt cgg aca aaa     1584
Tyr Leu Lys Gln Ala Pro Pro Ser Lys Gly Pro Thr Val Arg Thr Lys
                515                 520                 525 aaa gta ggg aaa aac gaa gct gtc tta gag tgg gac caa ctt cct gtt     1632
Lys Val Gly Lys Asn Glu Ala Val Leu Glu Trp Asp Gln Leu Pro Val
    530                 535                 540 gat gtt cag aat gga ttt atc aga aat tat act ata ttt tat aga acc     1680
Asp Val Gln Asn Gly Phe Ile Arg Asn Tyr Thr Ile Phe Tyr Arg Thr
545                 550                 555                 560 atc att gga aat gaa act gct gtg aat gtg gat tct tcc cac aca gaa     1728
Ile Ile Gly Asn Glu Thr Ala Val Asn Val Asp Ser Ser His Thr Glu
                565                 570                 575 tat aca ttg tcc tct ttg act agt gac aca ttg tac atg gta cga atg     1776
Tyr Thr Leu Ser Ser Leu Thr Ser Asp Thr Leu Tyr Met Val Arg Met
            580                 585                 590 gca gca tac aca gat gaa ggt ggg aag gat ggt cca gaa ttc aga tct     1824
Ala Ala Tyr Thr Asp Glu Gly Gly Lys Asp Gly Pro Glu Phe Arg Ser
                595                 600                 605 tgt gac aaa act cac aca tgc cca ccg tgc cca gca cct gaa gcc gag     1872
Cys Asp Lys Thr His Thr Cys Pro Pro Cys Pro Ala Pro Glu Ala Glu
    610                 615                 620 ggc gcg ccg tca gtc ttc ctc ttc ccc cca aaa ccc aag gac acc ctc     1920
Gly Ala Pro Ser Val Phe Leu Phe Pro Pro Lys Pro Lys Asp Thr Leu
625                 630                 635                 640 atg atc tcc cgg acc cct gag gtc aca tgc gtg gtg gtg gac gtg agc     1968
Met Ile Ser Arg Thr Pro Glu Val Thr Cys Val Val Val Asp Val Ser
                645                 650                 655
```

```
cac gaa gac cct gag gtc aag ttc aac tgg tac gtg gac ggc gtg gag    2016
His Glu Asp Pro Glu Val Lys Phe Asn Trp Tyr Val Asp Gly Val Glu
            660                 665                 670 gtg cat aat gcc aag aca aag ccg cgg gag gag cag tac aac agc acg    2064
Val His Asn Ala Lys Thr Lys Pro Arg Glu Glu Gln Tyr Asn Ser Thr
675                 680                 685 tac cgt gtg gtc agc gtc ctc acc gtc ctg cac cag gac tgg ctg aat    2112
Tyr Arg Val Val Ser Val Leu Thr Val Leu His Gln Asp Trp Leu Asn
    690                 695                 700 ggc aag gag tac aag tgc aag gtc tcc aac aaa gcc ctc cca gcc ccc    2160
Gly Lys Glu Tyr Lys Cys Lys Val Ser Asn Lys Ala Leu Pro Ala Pro
705                 710                 715                 720 atc gag aaa acc atc tcc aaa gcc aaa ggg cag ccc cga gaa cca cag    2208
Ile Glu Lys Thr Ile Ser Lys Ala Lys Gly Gln Pro Arg Glu Pro Gln
            725                 730                 735 gtg tac acc ctg ccc cca tcc cgg gag gag atg acc aag aac cag gtc    2256
Val Tyr Thr Leu Pro Pro Ser Arg Glu Glu Met Thr Lys Asn Gln Val
                740                 745                 750 agc ctg acc tgc ctg gtc aaa ggc ttc tat ccc agc gac atc gcc gtg    2304
Ser Leu Thr Cys Leu Val Lys Gly Phe Tyr Pro Ser Asp Ile Ala Val
            755                 760                 765 gag tgg gag agc aat ggg cag ccg gag aac aac tac aag acc acg cct    2352
Glu Trp Glu Ser Asn Gly Gln Pro Glu Asn Asn Tyr Lys Thr Thr Pro
    770                 775                 780 ccc gtg ctg gac tcc gac ggc tcc ttc ttc ctc tat agc aag ctc acc    2400
Pro Val Leu Asp Ser Asp Gly Ser Phe Phe Leu Tyr Ser Lys Leu Thr
785                 790                 795                 800 gtg gac aag agc agg tgg cag cag ggg aac gtc ttc tca tgc tcc gtg    2448
Val Asp Lys Ser Arg Trp Gln Gln Gly Asn Val Phe Ser Cys Ser Val
            805                 810                 815 atg cat gag gct ctg cac aac cac tac acg cag aag agc ctc tcc ctg    2496
Met His Glu Ala Leu His Asn His Tyr Thr Gln Lys Ser Leu Ser Leu
                820                 825                 830 tct ccg ggt aaa tga                                                2511
Ser Pro Gly Lys
            835

<210> SEQ ID NO 11
<211> LENGTH: 836
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 11

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
                20                  25                  30

Pro Glu Ser Pro Val Val Gln Leu His Ser Asn Phe Thr Ala Val Cys
            35                  40                  45

Val Leu Lys Glu Lys Cys Met Asp Tyr Phe His Val Asn Ala Asn Tyr
        50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110
```

```
Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
    370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
        435                 440                 445

Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
```

-continued

```
                530                 535                 540
Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
                580                 585                 590

Ala Ala Tyr Thr Asp Glu Gly Gly Lys Asp Gly Pro Glu Phe Arg Ser
                595                 600                 605

Cys Asp Lys Thr His Thr Cys Pro Pro Cys Pro Ala Pro Glu Ala Glu
                610                 615                 620

Gly Ala Pro Ser Val Phe Leu Phe Pro Pro Lys Pro Lys Asp Thr Leu
625                 630                 635                 640

Met Ile Ser Arg Thr Pro Glu Val Thr Cys Val Val Val Asp Val Ser
                645                 650                 655

His Glu Asp Pro Glu Val Lys Phe Asn Trp Tyr Val Asp Gly Val Glu
                660                 665                 670

Val His Asn Ala Lys Thr Lys Pro Arg Glu Glu Gln Tyr Asn Ser Thr
                675                 680                 685

Tyr Arg Val Val Ser Val Leu Thr Val Leu His Gln Asp Trp Leu Asn
                690                 695                 700

Gly Lys Glu Tyr Lys Cys Lys Val Ser Asn Lys Ala Leu Pro Ala Pro
705                 710                 715                 720

Ile Glu Lys Thr Ile Ser Lys Ala Lys Gly Gln Pro Arg Glu Pro Gln
                725                 730                 735

Val Tyr Thr Leu Pro Pro Ser Arg Glu Glu Met Thr Lys Asn Gln Val
                740                 745                 750

Ser Leu Thr Cys Leu Val Lys Gly Phe Tyr Pro Ser Asp Ile Ala Val
                755                 760                 765

Glu Trp Glu Ser Asn Gly Gln Pro Glu Asn Asn Tyr Lys Thr Thr Pro
                770                 775                 780

Pro Val Leu Asp Ser Asp Gly Ser Phe Phe Leu Tyr Ser Lys Leu Thr
785                 790                 795                 800

Val Asp Lys Ser Arg Trp Gln Gln Gly Asn Val Phe Ser Cys Ser Val
                805                 810                 815

Met His Glu Ala Leu His Asn His Tyr Thr Gln Lys Ser Leu Ser Leu
                820                 825                 830

Ser Pro Gly Lys
        835
```

<210> SEQ ID NO 12
<211> LENGTH: 2511
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(2508)

<400> SEQUENCE: 12

```
atg ctg aca ctg cag aca tgg ctg gtg cag gcc ctg ttt atc ttt ctg      48
Met Leu Thr Leu Gln Thr Trp Leu Val Gln Ala Leu Phe Ile Phe Leu
 1               5                  10                  15 acc acc gag tct aca gga gag ctg ctg gat cct tgc ggc tat atc tcc      96
Thr Thr Glu Ser Thr Gly Glu Leu Leu Asp Pro Cys Gly Tyr Ile Ser
             20                  25                  30
```

```
cct gag tct cct gtg gtg cag ctg cat tct aac ttc acc gcc gtg tgt       144
Pro Glu Ser Pro Val Val Gln Leu His Ser Asn Phe Thr Ala Val Cys
         35                  40                  45 gtg ctg aag gaa aag tgc atg gac tac ttc cac gtg aac gcc aac tac       192
Val Leu Lys Glu Lys Cys Met Asp Tyr Phe His Val Asn Ala Asn Tyr
 50                  55                  60 atc gtg tgg aaa acc aac cac ttc acc atc ccc aag gag cag tac acc       240
Ile Val Trp Lys Thr Asn His Phe Thr Ile Pro Lys Glu Gln Tyr Thr
 65                  70                  75                  80 atc atc aac cgg acc gct tct tct gtg acc ttc acc gat atc gcc tcc       288
Ile Ile Asn Arg Thr Ala Ser Ser Val Thr Phe Thr Asp Ile Ala Ser
                     85                  90                  95 ctg aat atc cag ctg acc tgc aac atc ctg acc ttt gga cag ctg gag       336
Leu Asn Ile Gln Leu Thr Cys Asn Ile Leu Thr Phe Gly Gln Leu Glu
                 100                 105                 110 cag aat gtg tac ggc atc acc atc atc tct ggc ctg cct cca gag aag       384
Gln Asn Val Tyr Gly Ile Thr Ile Ile Ser Gly Leu Pro Pro Glu Lys
             115                 120                 125 cct aag aac ctg tcc tgc atc gtg aat gag ggc aag aag atg agg tgt       432
Pro Lys Asn Leu Ser Cys Ile Val Asn Glu Gly Lys Lys Met Arg Cys
130                 135                 140 gag tgg gat ggc ggc aga gag aca cat ctg gag acc aac ttc acc ctg       480
Glu Trp Asp Gly Gly Arg Glu Thr His Leu Glu Thr Asn Phe Thr Leu
145                 150                 155                 160 aag tct gag tgg gcc acc cac aag ttt gcc gac tgc aag gcc aag aga       528
Lys Ser Glu Trp Ala Thr His Lys Phe Ala Asp Cys Lys Ala Lys Arg
                 165                 170                 175 gat acc cct acc tct tgc acc gtg gac tac tcc acc gtg tac ttc gtg       576
Asp Thr Pro Thr Ser Cys Thr Val Asp Tyr Ser Thr Val Tyr Phe Val
             180                 185                 190 aac atc gag gtg tgg gtg gag gct gag aat gct ctg ggc aag gtg acc       624
Asn Ile Glu Val Trp Val Glu Ala Glu Asn Ala Leu Gly Lys Val Thr
         195                 200                 205 tct gac cac atc aac ttc gac ccc gtg tac aag gtg aag cct aac cct       672
Ser Asp His Ile Asn Phe Asp Pro Val Tyr Lys Val Lys Pro Asn Pro
 210                 215                 220 cct cac aac ctg tcc gtg atc aac tct gag gag ctg tcc tct atc ctg       720
Pro His Asn Leu Ser Val Ile Asn Ser Glu Glu Leu Ser Ser Ile Leu
225                 230                 235                 240 aag ctg acc tgg acc aac cct tcc atc aag tcc gtg atc atc ctg aag       768
Lys Leu Thr Trp Thr Asn Pro Ser Ile Lys Ser Val Ile Ile Leu Lys
                 245                 250                 255 tac aac atc cag tac agg acc aag gat gct tct acc tgg tct cag atc       816
Tyr Asn Ile Gln Tyr Arg Thr Lys Asp Ala Ser Thr Trp Ser Gln Ile
             260                 265                 270 cct cct gag gat acc gct tcc acc aga tcc agc ttc aca gtg cag gac       864
Pro Pro Glu Asp Thr Ala Ser Thr Arg Ser Ser Phe Thr Val Gln Asp
         275                 280                 285 ctg aag cct ttt acc gag tac gtg ttc agg atc cgg tgc atg aag gag       912
Leu Lys Pro Phe Thr Glu Tyr Val Phe Arg Ile Arg Cys Met Lys Glu
 290                 295                 300 gat ggc aag ggc tat tgg tct gac tgg tct gag gag gct tct ggc atc       960
Asp Gly Lys Gly Tyr Trp Ser Asp Trp Ser Glu Glu Ala Ser Gly Ile
305                 310                 315                 320 acc tac gag gac aga cct tct aag gcc cct agc ttc tgg tac aag atc      1008
Thr Tyr Glu Asp Arg Pro Ser Lys Ala Pro Ser Phe Trp Tyr Lys Ile
                 325                 330                 335 gac cct tct cac acc cag ggc tat aga aca gtg cag ctg gtg tgg aaa      1056
Asp Pro Ser His Thr Gln Gly Tyr Arg Thr Val Gln Leu Val Trp Lys
             340                 345                 350
```

```
acc ctg cct cca ttc gag gct aat ggc aag atc ctg gac tat gag gtg        1104
Thr Leu Pro Pro Phe Glu Ala Asn Gly Lys Ile Leu Asp Tyr Glu Val
        355                 360                 365 acc ctg acc aga tgg aag tct cac ctg cag aac tac acc gtg aac gct        1152
Thr Leu Thr Arg Trp Lys Ser His Leu Gln Asn Tyr Thr Val Asn Ala
370                 375                 380 acc aag ctg acc gtg aac ctg acc aac gat aga tac ctg gct acc ctg        1200
Thr Lys Leu Thr Val Asn Leu Thr Asn Asp Arg Tyr Leu Ala Thr Leu
385                 390                 395                 400 acc gtg aga aat ctg gtg ggc aag tct gat gct gct gtg ctg acc atc        1248
Thr Val Arg Asn Leu Val Gly Lys Ser Asp Ala Ala Val Leu Thr Ile
                405                 410                 415 cct gcc tgt gat ttt cag gct acc cac cct gtg atg gat ctg aag gcc        1296
Pro Ala Cys Asp Phe Gln Ala Thr His Pro Val Met Asp Leu Lys Ala
            420                 425                 430 ttc ccc aag gat aac atg ctg tgg gtg gag tgg aca aca cct aga gag        1344
Phe Pro Lys Asp Asn Met Leu Trp Val Glu Trp Thr Thr Pro Arg Glu
        435                 440                 445 tcc gtg aag aag tac atc ctg gag tgg tgc gtg ctg tct gat aag gcc        1392
Ser Val Lys Lys Tyr Ile Leu Glu Trp Cys Val Leu Ser Asp Lys Ala
450                 455                 460 cct tgc atc aca gat tgg cag cag gag gat ggc acc gtg cat aga acc        1440
Pro Cys Ile Thr Asp Trp Gln Gln Glu Asp Gly Thr Val His Arg Thr
465                 470                 475                 480 tac ctg aga ggc aat ctg gcc gag tct aag tgc tat ctg atc acc gtg        1488
Tyr Leu Arg Gly Asn Leu Ala Glu Ser Lys Cys Tyr Leu Ile Thr Val
                485                 490                 495 acc cct gtg tat gct gat gga cct ggc tct cct gag tct atc aag gcc        1536
Thr Pro Val Tyr Ala Asp Gly Pro Gly Ser Pro Glu Ser Ile Lys Ala
            500                 505                 510 tac ctg aag cag gct cct cca tct aag gga cct acc gtg agg aca aag        1584
Tyr Leu Lys Gln Ala Pro Pro Ser Lys Gly Pro Thr Val Arg Thr Lys
        515                 520                 525 aag gtg ggc aag aac gag gct gtg ctg gag tgg gat cag ctg cct gtg        1632
Lys Val Gly Lys Asn Glu Ala Val Leu Glu Trp Asp Gln Leu Pro Val
530                 535                 540 gat gtg cag aac ggc ttc atc cgg aac tac acc atc ttc tac cgg acc        1680
Asp Val Gln Asn Gly Phe Ile Arg Asn Tyr Thr Ile Phe Tyr Arg Thr
545                 550                 555                 560 atc atc ggc aat gag acc gcc gtg aac gtg gat tct tcc cac acc gag        1728
Ile Ile Gly Asn Glu Thr Ala Val Asn Val Asp Ser Ser His Thr Glu
                565                 570                 575 tac aca ctg tcc tct ctg acc tct gac acc ctg tac atg gtg aga atg        1776
Tyr Thr Leu Ser Ser Leu Thr Ser Asp Thr Leu Tyr Met Val Arg Met
            580                 585                 590 gcc gct tat acc gat gag ggc ggc aag gat gga cct gag ttc aga tcc        1824
Ala Ala Tyr Thr Asp Glu Gly Gly Lys Asp Gly Pro Glu Phe Arg Ser
        595                 600                 605 tgc gac aag acc cac acc tgt cct cct tgt cct gct cct gag gct gag        1872
Cys Asp Lys Thr His Thr Cys Pro Pro Cys Pro Ala Pro Glu Ala Glu
610                 615                 620 ggc gct cct tct gtg ttt ctg ttc ccc cca aag cct aag gat acc ctg        1920
Gly Ala Pro Ser Val Phe Leu Phe Pro Pro Lys Pro Lys Asp Thr Leu
625                 630                 635                 640 atg atc tcc aga acc cct gag gtg aca tgt gtg gtg gat gtg tct        1968
Met Ile Ser Arg Thr Pro Glu Val Thr Cys Val Val Asp Val Ser
                645                 650                 655 cat gag gac ccc gag gtg aag ttc aac tgg tac gtg gat ggc gtg gag        2016
His Glu Asp Pro Glu Val Lys Phe Asn Trp Tyr Val Asp Gly Val Glu
            660                 665                 670
```

```
gtg cac aat gct aag acc aag cct agg gag gag cag tac aac tcc acc   2064
Val His Asn Ala Lys Thr Lys Pro Arg Glu Glu Gln Tyr Asn Ser Thr
            675                 680                 685 tac aga gtg gtg tct gtg ctg aca gtg ctg cat cag gat tgg ctg aac   2112
Tyr Arg Val Val Ser Val Leu Thr Val Leu His Gln Asp Trp Leu Asn
        690                 695                 700 ggc aag gag tac aag tgc aag gtg tcc aac aag gct ctg cct gct cct   2160
Gly Lys Glu Tyr Lys Cys Lys Val Ser Asn Lys Ala Leu Pro Ala Pro
705                 710                 715                 720 atc gaa aag acc atc tcc aag gct aag gga cag cct aga gag cct cag   2208
Ile Glu Lys Thr Ile Ser Lys Ala Lys Gly Gln Pro Arg Glu Pro Gln
                725                 730                 735 gtg tac aca ctg cct cca tct agg gag gag atg acc aag aat cag gtg   2256
Val Tyr Thr Leu Pro Pro Ser Arg Glu Glu Met Thr Lys Asn Gln Val
            740                 745                 750 tcc ctg acc tgt ctg gtg aag ggc ttc tac cct tct gat atc gct gtg   2304
Ser Leu Thr Cys Leu Val Lys Gly Phe Tyr Pro Ser Asp Ile Ala Val
        755                 760                 765 gag tgg gag tct aat ggc cag ccc gag aac aat tac aag acc acc cct   2352
Glu Trp Glu Ser Asn Gly Gln Pro Glu Asn Asn Tyr Lys Thr Thr Pro
    770                 775                 780 cct gtg ctg gat tct gac ggc tcc ttc ttc ctg tac tcc aaa ctg acc   2400
Pro Val Leu Asp Ser Asp Gly Ser Phe Phe Leu Tyr Ser Lys Leu Thr
785                 790                 795                 800 gtg gac aag tct aga tgg cag cag ggc aac gtg ttc tct tgt tcc gtg   2448
Val Asp Lys Ser Arg Trp Gln Gln Gly Asn Val Phe Ser Cys Ser Val
                805                 810                 815 atg cac gag gct ctg cac aat cac tat acc cag aag tcc ctg tct ctg   2496
Met His Glu Ala Leu His Asn His Tyr Thr Gln Lys Ser Leu Ser Leu
            820                 825                 830 tct cct ggc aag tga                                                2511
Ser Pro Gly Lys
        835

<210> SEQ ID NO 13
<211> LENGTH: 836
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 13

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125
```

-continued

```
Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
    370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
        435                 440                 445

Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560
```

```
Ile Ile Gly Asn Glu Thr Ala Val Asn Val Asp Ser Ser His Thr Glu
                565                 570                 575
Tyr Thr Leu Ser Ser Leu Thr Ser Asp Thr Leu Tyr Met Val Arg Met
            580                 585                 590
Ala Ala Tyr Thr Asp Glu Gly Gly Lys Asp Gly Pro Glu Phe Arg Ser
        595                 600                 605
Cys Asp Lys Thr His Thr Cys Pro Pro Cys Pro Ala Pro Glu Ala Glu
    610                 615                 620
Gly Ala Pro Ser Val Phe Leu Phe Pro Pro Lys Pro Lys Asp Thr Leu
625                 630                 635                 640
Met Ile Ser Arg Thr Pro Glu Val Thr Cys Val Val Val Asp Val Ser
                645                 650                 655
His Glu Asp Pro Glu Val Lys Phe Asn Trp Tyr Val Asp Gly Val Glu
            660                 665                 670
Val His Asn Ala Lys Thr Lys Pro Arg Glu Glu Gln Tyr Asn Ser Thr
        675                 680                 685
Tyr Arg Val Val Ser Val Leu Thr Val Leu His Gln Asp Trp Leu Asn
    690                 695                 700
Gly Lys Glu Tyr Lys Cys Lys Val Ser Asn Lys Ala Leu Pro Ala Pro
705                 710                 715                 720
Ile Glu Lys Thr Ile Ser Lys Ala Lys Gly Gln Pro Arg Glu Pro Gln
                725                 730                 735
Val Tyr Thr Leu Pro Pro Ser Arg Glu Glu Met Thr Lys Asn Gln Val
            740                 745                 750
Ser Leu Thr Cys Leu Val Lys Gly Phe Tyr Pro Ser Asp Ile Ala Val
        755                 760                 765
Glu Trp Glu Ser Asn Gly Gln Pro Glu Asn Asn Tyr Lys Thr Thr Pro
    770                 775                 780
Pro Val Leu Asp Ser Asp Gly Ser Phe Phe Leu Tyr Ser Lys Leu Thr
785                 790                 795                 800
Val Asp Lys Ser Arg Trp Gln Gln Gly Asn Val Phe Ser Cys Ser Val
                805                 810                 815
Met His Glu Ala Leu His Asn His Tyr Thr Gln Lys Ser Leu Ser Leu
            820                 825                 830
Ser Pro Gly Lys
        835

<210> SEQ ID NO 14
<211> LENGTH: 2511
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 14
atgctgacac tgcagacatg gctggtgcag gccctgttta tctttctgac caccgagtct      60
acaggagagc tgctggatcc ttgcggctat atctccctg agtctcctgt ggtgcagctg      120
cattctaact tcaccgccgt gtgtgtgctg aaggaaaagt gcatggacta cttccacgtg      180
aacgccaact acatcgtgtg gaaaaccaac cacttcacca tccccaagga gcagtacacc      240
atcatcaacc ggaccgcttc ttctgtgacc ttcaccgata tcgcctccct gaatatccag      300
ctgacctgca acatcctgac ctttggacag ctggagcaga atgtgtacgg catcaccatc      360
atctctggcc tgcctccaga gaagcctaag aacctgtcct gcatcgtgaa tgagggcaag      420
```

| | |
|---|---|
| aagatgaggt gtgagtggga tggcggcaga gagacacatc tggagaccaa cttcaccctg | 480 |
| aagtctgagt gggccaccca caagtttgcc gactgcaagg ccaagagaga taccectacc | 540 |
| tcttgcaccg tggactactc caccgtgtac ttcgtgaaca tcgaggtgtg ggtggaggct | 600 |
| gagaatgctc tgggcaaggt gacctctgac cacatcaact tcgaccccgt gtacaaggtg | 660 |
| aagcctaacc ctcctcacaa cctgtccgtg atcaactctg aggagctgtc ctctatcctg | 720 |
| aagctgacct ggaccaaccc ttccatcaag tccgtgatca tcctgaagta caacatccag | 780 |
| tacaggacca aggatgcttc tacctggtct cagatccctc ctgaggatac cgcttccacc | 840 |
| agatccagct tcacagtgca ggacctgaag ccttttaccg agtacgtgtt caggatccgg | 900 |
| tgcatgaagg aggatggcaa gggctattgg tctgactggt ctgaggaggc ttctggcatc | 960 |
| acctacgagg acagaccttc taaggcccct agcttctggt acaagatcga cccttctcac | 1020 |
| acccagggct atagaacagt gcagctggtg tggaaaaccc tgcctccatt cgaggctaat | 1080 |
| ggcaagatcc tggactatga ggtgaccctg accagatgga agtctcacct gcagaactac | 1140 |
| accgtgaacg ctaccaagct gaccgtgaac ctgaccaacg atagatacct ggctaccctg | 1200 |
| accgtgagaa atctggtggg caagtctgat gctgctgtgc tgaccatccc tgcctgtgat | 1260 |
| tttcaggcta cccacctgt gatggatctg aaggccttcc ccaaggataa catgctgtgg | 1320 |
| gtggagtgga caacacctag agagtccgtg aagaagtaca tcctggagtg gtgcgtgctg | 1380 |
| tctgataagg ccccttgcat cacagattgg cagcaggagg atggcaccgt gcatagaacc | 1440 |
| tacctgagag gcaatctggc cgagtctaag tgctatctga tcaccgtgac ccctgtgtat | 1500 |
| gctgatggac ctggctctcc tgagtctatc aaggcctacc tgaagcaggc tcctccatct | 1560 |
| aagggaccta ccgtgaggac aaagaaggtg ggcaagaacg aggctgtgct ggagtgggat | 1620 |
| cagctgcctg tggatgtgca gaacggcttc atccggaact acaccatctt ctaccggacc | 1680 |
| atcatcggca tgagaccgc cgtgaacgtg gattcttccc acaccgagta cacactgtcc | 1740 |
| tctctgacct ctgacaccct gtacatggtg agaatggccg cttataccga tgagggcggc | 1800 |
| aaggatggac ctgagttcag atcctgcgac aagacccaca cctgtcctcc ttgtcctgct | 1860 |
| cctgaggctg agggcgctcc ttctgtgttt ctgttccccc caaagcctaa ggataccctg | 1920 |
| atgatctcca gaacccctga ggtgacatgt gtggtggtgg atgtgtctca tgaggaccc | 1980 |
| gaggtgaagt tcaactggta cgtggatggc gtggaggtgc acaatgctaa gaccaagcct | 2040 |
| agggaggagc agtacaactc cacctacaga gtggtgtctg tgctgacagt gctgcatcag | 2100 |
| gattggctga acggcaagga gtacaagtgc aaggtgtcca acaaggctct gcctgctcct | 2160 |
| atcgaaaaga ccatctccaa ggctaaggga cagcctagag agcctcaggt gtacacactg | 2220 |
| cctccatcta gggaggagat gaccaagaat caggtgtccc tgacctgtct ggtgaagggc | 2280 |
| ttctacccctt ctgatatcgc tgtggagtgg gagtctaatg gccagcccga gaacaattac | 2340 |
| aagaccaccc ctcctgtgct ggattctgac ggctcctct tcctgtactc caaactgacc | 2400 |
| gtggacaagt ctagatggca gcagggcaac gtgttctctt gttccgtgat gcacgaggct | 2460 |
| ctgcacaatc actatacccca gaagtccctg tctctgtctc ctggcaagtg a | 2511 |

<210> SEQ ID NO 15
<211> LENGTH: 2511
<212> TYPE: DNA
<213> ORGANISM: Artificial Sequence
<220> FEATURE:
<223> OTHER INFORMATION: Description of Artificial Sequence: Synthetic construct

<400> SEQUENCE: 15

-continued

```
atgctgaccc tgcagacctg gctggtgcag gccctgttca tcttcctgac caccgagagc      60
accggcgagc tgctggaccc ctgcggctac atcagcccg agagcccgt ggtgcagctg       120 cacagcaact tcaccgccgt gtgcgtgctg aaggagaagt gcatggacta cttccacgtg      180
aacgccaact acatcgtgtg aagaccaac cacttcacca tccccaagga gcagtacacc       240
atcatcaacc gcaccgccag cagcgtgacc ttcaccgaca tcgccagcct gaacatccag      300
ctgacctgca catcctgac cttcggccag ctggagcaga acgtgtacgg catcaccatc       360
atcagcggcc tgcccccga aagcccaag aacctgagct gcatcgtgaa cgagggcaag       420
aagatgcgct gcgagtggga cggcggccgc gagacccacc tggagaccaa cttcaccctg      480
aagagcgagt gggccaccca caagttcgcc gactgcaagg ccaagcgcga cccccccacc      540
agctgcaccg tggactacag caccgtgtac ttcgtgaaca tcgaggtgtg ggtggaggcc      600
gagaacgccc tggcaaggt gaccagcgac cacatcaact tcgaccccgt gtacaaggtg      660
aagcccaacc cccccacaa cctgagcgtg atcaacagcg aggagctgag cagcatcctg      720
aagctgacct ggaccaaccc cagcatcaag agcgtgatca tcctgaagta caacatccag      780
taccgcacca aggacgccag cacctggagc cagatccccc cgaggacac cgccagcacc       840 cgcagcagct tcaccgtgca ggacctgaag cccttcaccg agtacgtgtt ccgcatccgc      900
tgcatgaagg aggacggcaa gggctactgg agcgactgga gcgaggaggc cagcggcatc      960
acctacgagg accgcccag caaggcccc agcttctggt acaagatcga ccccagccac      1020
acccagggct accgcaccgt gcagctggtg tggaagaccc tgccccctt cgaggccaac      1080 ggcaagatcc tggactacga ggtgaccctg accgctgga agagccacct gcagaactac       1140
accgtgaacg ccaccaagct gaccgtgaac ctgaccaacg accgctacct ggccaccctg      1200
accgtgcgca acctggtggg caagagcgac gccgccgtgc tgaccatccc cgcctgcgac      1260
ttccaggcca cccaccccgt gatggacctg aaggccttcc ccaaggacaa catgctgtgg      1320
gtggagtgga ccacccccg cgagagcgtg aagaagtaca tcctggagtg gtgcgtgctg      1380
agcgacaagg cccctgcat caccgactgg cagcaggagg acggcaccgt gcaccgcacc      1440
tacctgcgcg gcaacctggc cgagagcaag tgctacctga tcaccgtgac ccccgtgtac      1500
gccgacggcc ccggcagccc cgagagcatc aaggcctacc tgaagcaggc cccccccagc      1560
aagggcccca ccgtgcgcac caagaaggtg ggcaagaacg aggccgtgct ggagtgggac      1620
cagctgcccg tggacgtgca gaacggcttc atccgcaact acaccatctt ctaccgcacc      1680
atcatcggca acgagaccgc cgtgaacgtg gacagcagcc acaccgagta caccctgagc      1740
agcctgacca cgacaccct gtacatggtg cgcatggccg cctacaccga cgagggcggc      1800
aaggacggcc ccgagttccg cagctgcgac aagacccaca cctgccccc ctgccccgcc      1860 cccgaggccg agggcggccc cagcgtgttc ctgttccccc ccaagcccaa ggacaccctg      1920
atgatcagcc gcaccccga ggtgacctgc gtggtggtgg acgtgagcca cgaggacccc      1980
gaggtgaagt tcaactggta cgtggacggc gtggaggtgc acaacgccaa gaccaagccc      2040
cgcgaggagc agtacaacag cacctaccgc gtggtgagcg tgctgaccgt gctgcaccag      2100
gactggctga acggcaagga gtacaagtgc aaggtgagca caaggccct gcccgcccc      2160 atcgagaaga ccatcagcaa ggccaagggc cagccccgcg agccccaggt gtacaccctg      2220
cccccccagc cgcgaggagat gaccaagaac caggtgagcc tgacctgcct ggtgaagggc      2280
ttctacccca gcgacatcgc cgtggagtgg gagagcaacg ccagccgga aacaactac      2340 aagaccaccc ccccgtgct ggacagcgac ggcagcttct tcctgtacag caagctgacc      2400
```

```
gtggacaaga gccgctggca gcagggcaac gtgttcagct gcagcgtgat gcacgaggcc    2460
ctgcacaacc actacaccca agagagcctg agcctgagcc ccggcaagta a            2511

<210> SEQ ID NO 16
<211> LENGTH: 2511
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 16
atgctgacac tccagacgtg gctcgtgcag gcactattca ttttcctcac tacggagtct      60
acaggcgagc tgctggaccc ctgcggctat atttcccccg agtctcccgt ggtgcagctg     120
cactcgaatt tcacggccgt atgcgtcctc aaggagaagt gcatggatta ctttcacgtg     180
aatgcaaatt atatcgtttg gaaaacgaac cactttacca tccccaagga acagtacaca     240
atcatcaacc gcacagcatc gagtgtgacc ttcaccgaca ttgcgtccct caatatccag     300
ctgacctgca acatcctgac atttgggcag ctggagcaga acgtttacgg catcactatc     360
atctcggggc tcccccctga aagccaaag aacctctcct gtatcgttaa cgagggaaag     420
aagatgaggt gcgagtggga tggggccgg agagacccacc tggagacgaa cttcaccctg     480
aagtcggagt gggcgacgca caagtttgcg gattgcaagg ccaaaaggga tacacccacc     540
agctgtactg tcgactactc aacggtttac tttgtcaaca tagaggtttg ggtgaggcg     600 gagaacgccc tgggcaaggt gacctccgac cacatcaatt tcgatcccgt gtataaagtg     660
aaacctaacc cgccccacaa tctcagtgta attaactccg aggagctcag ttctatcctt     720
aagttgactt ggaccaaccc ttccatcaag agcgtaatca tcctgaagta caacattcag     780
taccgtacta aggacgcgtc cacatggagc cagatccccc ctgaggatac cgcatccacc     840
cggtcgagtt ttaccgtgca ggacctgaaa cccttcaccg agtacgtgtt ccgcatccgg     900
tgcatgaaag aggacgggaa ggggtactgg tccgattggt ccgaggaggc cagtggcatt     960
acctatgaag accggcctag taaggccccc tccttctggt ataaaatcga cccgtcccac    1020
acccagggct accgcaccgt gcagttggtg tggaagacgc tgccgccatt cgaggccaac    1080
gggaagattc tggactacga ggtcaccctg actcgctgga atcccaccct ccagaattat    1140
accgtgaacg ccacgaagct caccgttaac ctgacgaacg accgctatct ggccaccctg    1200
accgtgcgca acctggtggg caagtccgac gctgcagtgc tgaccatccc ggcatgtgac    1260
ttccaggcga cacacccgt gatggatctg aaggcgtttc ctaaggataa tatgctgtgg    1320
gtggagtgga cgaccccccg agagtccgtg aagaaataca ttctggagtg gtgcgtgctg    1380
agcgacaagg cccccttgca taccgattgg caacaagagg acggtaccgt ccaccgaacc    1440
tacctgaggg ggaacctcgc tgagtccaag tgctacctaa tcacggtgac cccagtgtac    1500
gccgatggtc cagggtcccc tgagtccatc aaggcctacc tcaagcaggc cccaccttcg    1560
aagggcccta cagtgagaac caagaaggtc gggaagaacg aggcggtgct ggaatgggac    1620
cagctgccag tggacgtgca gaatggcttc atccgaaatt acaccatctt ctaccggacc    1680
atcatcggca tgagaccgc cgtcaacgta gactcctccc cacccgagta cacgctgtcc    1740
tcactgacta gcgacacccct gtatatggtt cgcatggctg cttacaccga tgaaggcggg    1800
aaagacggcc ctgagttcag gtcctgtgac aagactcata cgtgcccccc atgtcctgcc    1860
ccggaagccg aggggggtcc ctccgtgttc ctcttccccc ccaagccgaa agacaccctc    1920
```

```
atgatctcac ggacccccga ggtgacatgc gtggtggtgg atgtgtcaca cgaggacccc      1980
gaagtcaagt tcaactggta cgtggacggc gtggaggtcc acaatgccaa gaccaagcca      2040
cgggaggagc agtacaattc cacctacaga gtagtcagtg tgctgaccgt cctccaccag      2100
gactggctca acggcaaaga gtacaagtgc aaggtgtcca acaaggccct gccagccccg      2160
atcgagaaaa ccatttccaa ggccaagggt cagcccaggg agcctcaggt ctacacgctg      2220
cctccgtcca gagaggaaat gaccaagaat caggtgtcgc tgacttgcct cgtgaaaggg      2280
ttctacccca gcgacatcgc tgtggagtgg gagtcgaacg ggcagcctga gaataattat      2340
aagacaaccc cccccgtgct ggactccgac ggctccttt tcctctactc taagctgacc      2400
gtggacaaga gtaggtggca gcaggggaac gtcttctctt gttcggtcat gcacgaggcc      2460
ctccacaacc attatactca gaagtccctg tcgctcagtc ccggtaaatg a               2511
```

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 17

His His His His His His
 1               5

OPTIMIZED NUCLEOTIDE SEQUENCES ENCODING SGP130

CROSS-REFERENCE TO RELATED APPLICATIONS

This application is the National Stage Entry of International Application PCT/EP05/09247 filed on Aug. 26, 2005, which claims priority to European Patent Application 04020455.4 filed on Aug. 27, 2004. All of the above-referenced patent applications are hereby incorporated by reference in their entirety for all purposes.

The present invention relates to codon optimized sgp130 encoding nucleic acid molecules as well as a method for the highly efficient recombinant production of sgp130 in mammalian cells or bacteria using a nucleic acid molecule of the invention.

For the treatment of various diseases such as Crohn's disease etc. the specific blocking of IL-6 responses dependent on soluble IL-6R might be desirable for treatment. It was found that a soluble gp130-dimer, in particular an IgG-Fc fusion protein or a PEGylated version of sgp130, efficiently inhibits the anti-apoptotic effect of sIL-6R from LPMC from Crohn's disease (CD) patients and that, thus, said compound is useful for the treatment of said disease and related diseases like, e.g., colitis or rheumatoid arthritis. Unfortunately, so far the recombinant production of sgp130 is difficult in particular due to the fact that only low amounts of protein can be obtained Thus, the technical problem underlying the present invention was to provide means allowing to improve the efficiency of recombinant production of sgp130Fc or sgp130(D1-D3).

The solution of the said technical problem is achieved by providing the embodiments characterized in the claims. During the experiments leading to the present invention it was found that by use of particular codon optimized versions of the DNA encoding sgp130Fc the yields of recombinant protein can be increased at least 10- to 20-fold compared to the unmodified version of the DNA. In case of the prokaryotic sgp130 (D1-D39 version, the optimization of the DNA led to the reduction of undesired shorter side products.

Grey shedding marks the parts of the protein which have been optimized. (A) Eukaryotic construct comprising a signal peptide, six extracellular gp130 domains and the IgG-Fc part. (B) Variations of the sgp130 protein expressed in prokaryotic cells. sgp130 can be expressed with or without N-terminal leader sequence and/or C-terminal Tag for purification purposes.

Figure 2A:
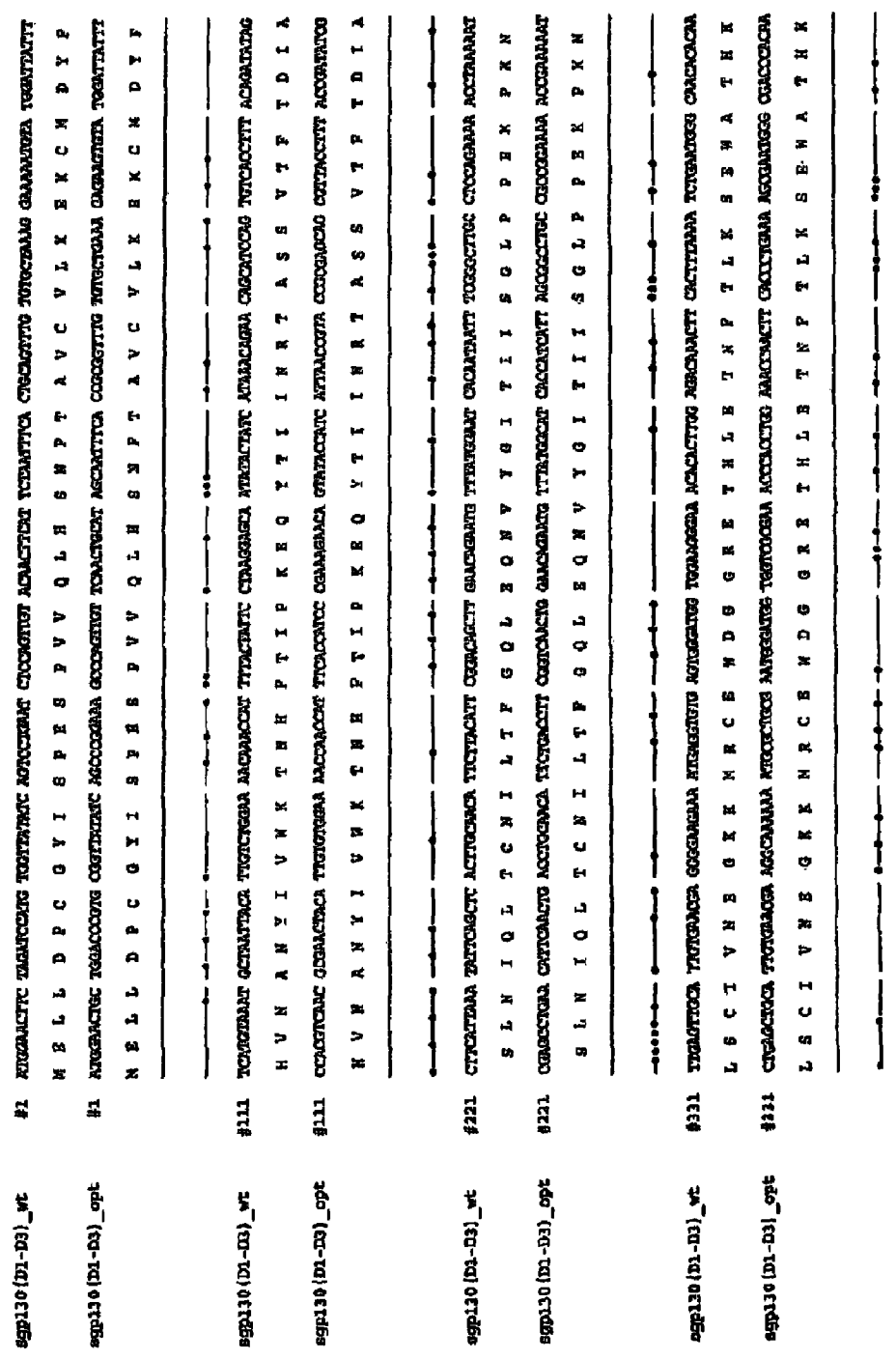
Figure 2B:
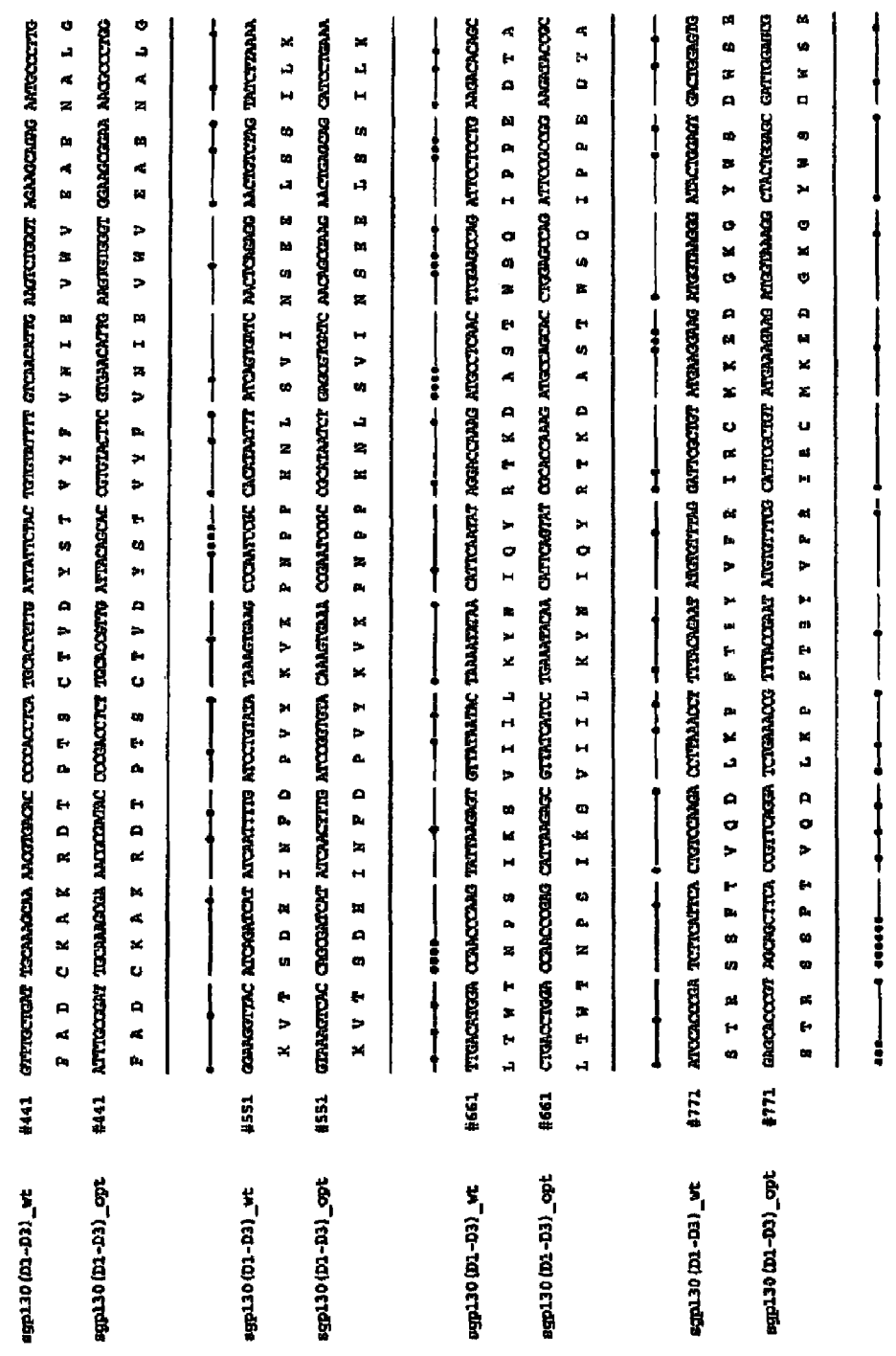
Figure 2C:
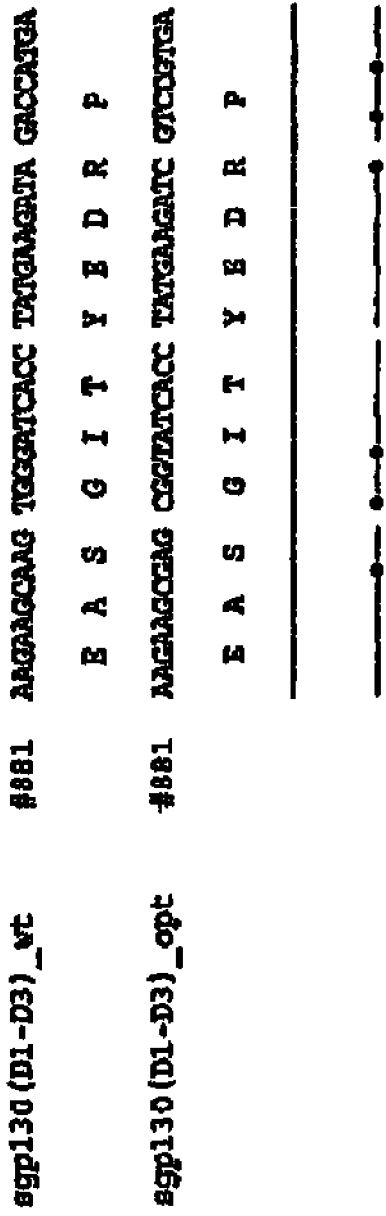
Figure 3F:

FIGS. 2A, 2B and 2C: sgp130(D1-D3) (Nucleotide Sequence and Amino Acid Sequence) for Expression in Bacterial Cells An alignment of the nucleotide sequence (SEQ ID NO: 6) with optimized codons (sgp130(D1-D3)_opt) vs. the original sequence (SEQ ID NO: 7) (sgp130(D1-D3)_wt) is shown. Amino acid sequences disclosed as SEQ ID NOS 8-9, respectively, in order of appearance.

Figure 3A:
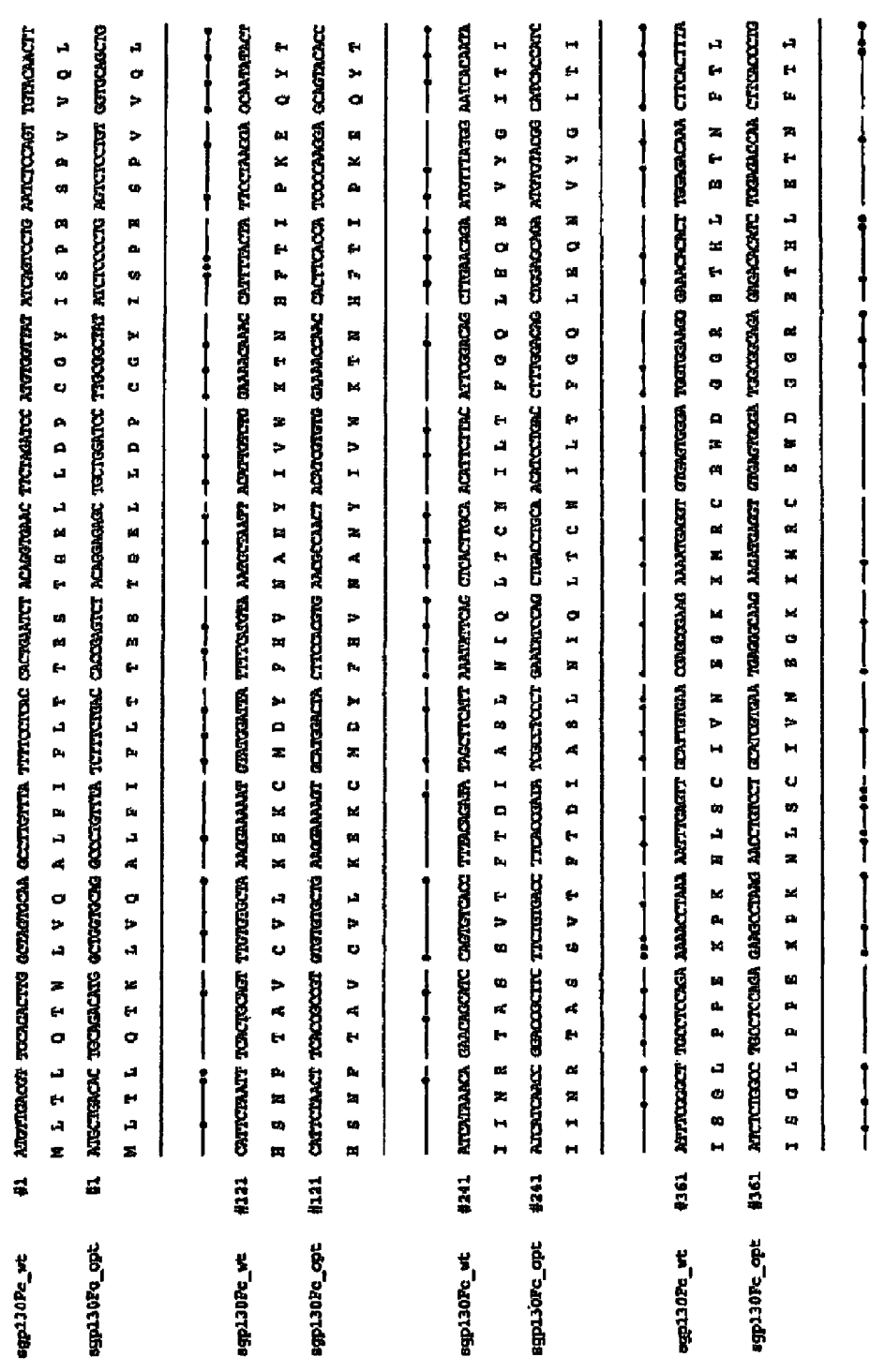
Figure 3B:
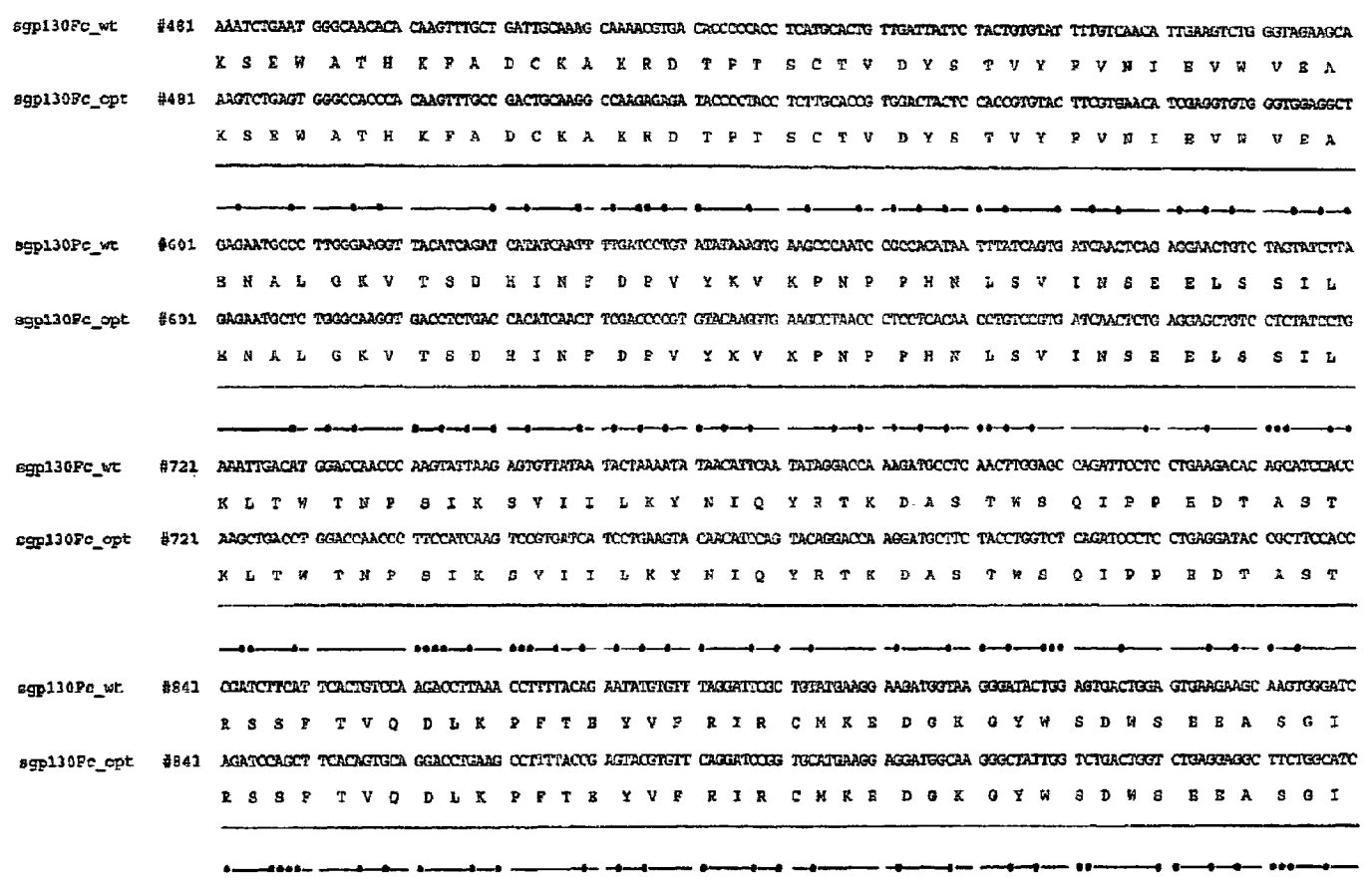
Figure 3C:
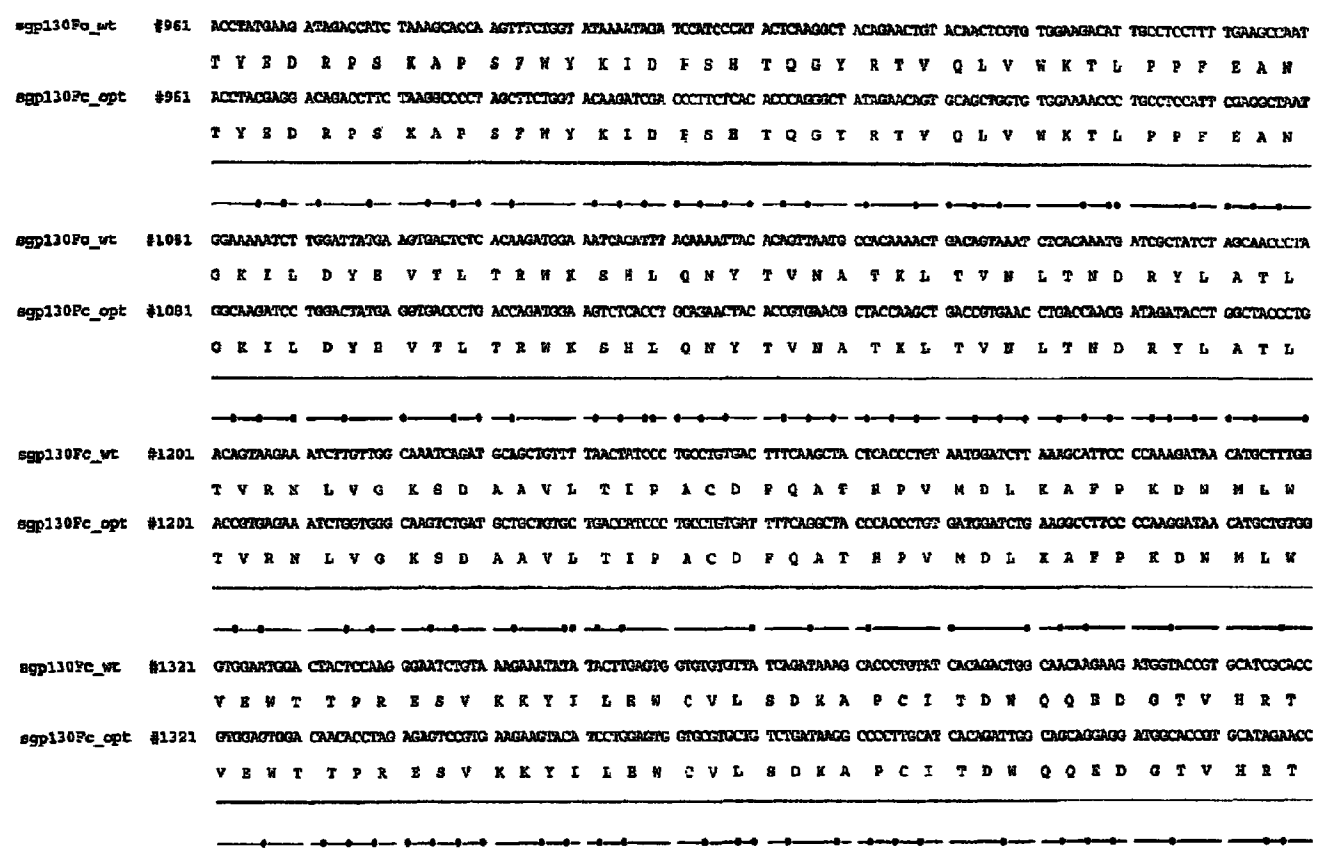
Figure 3D:
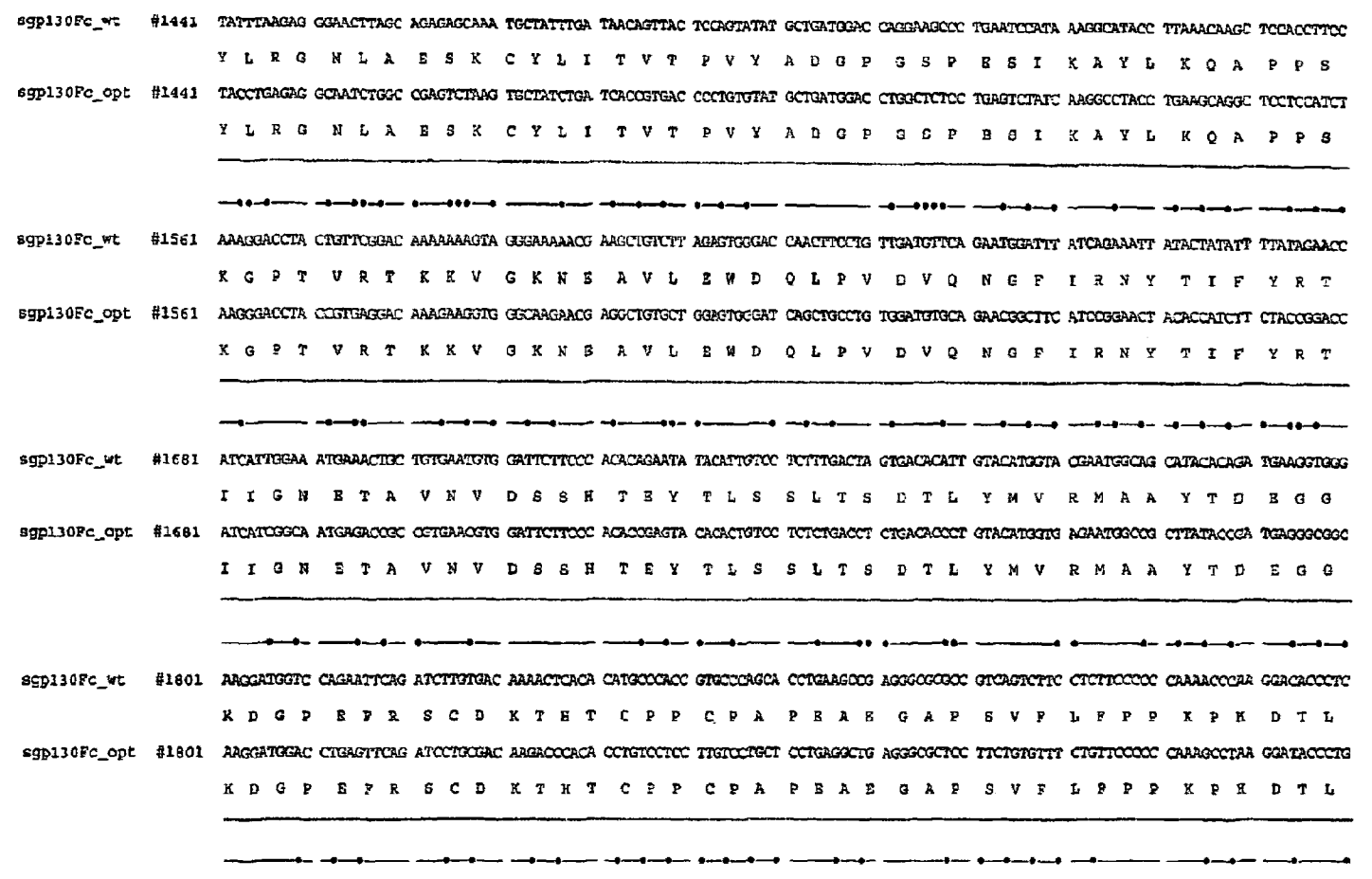
Figure 3E:
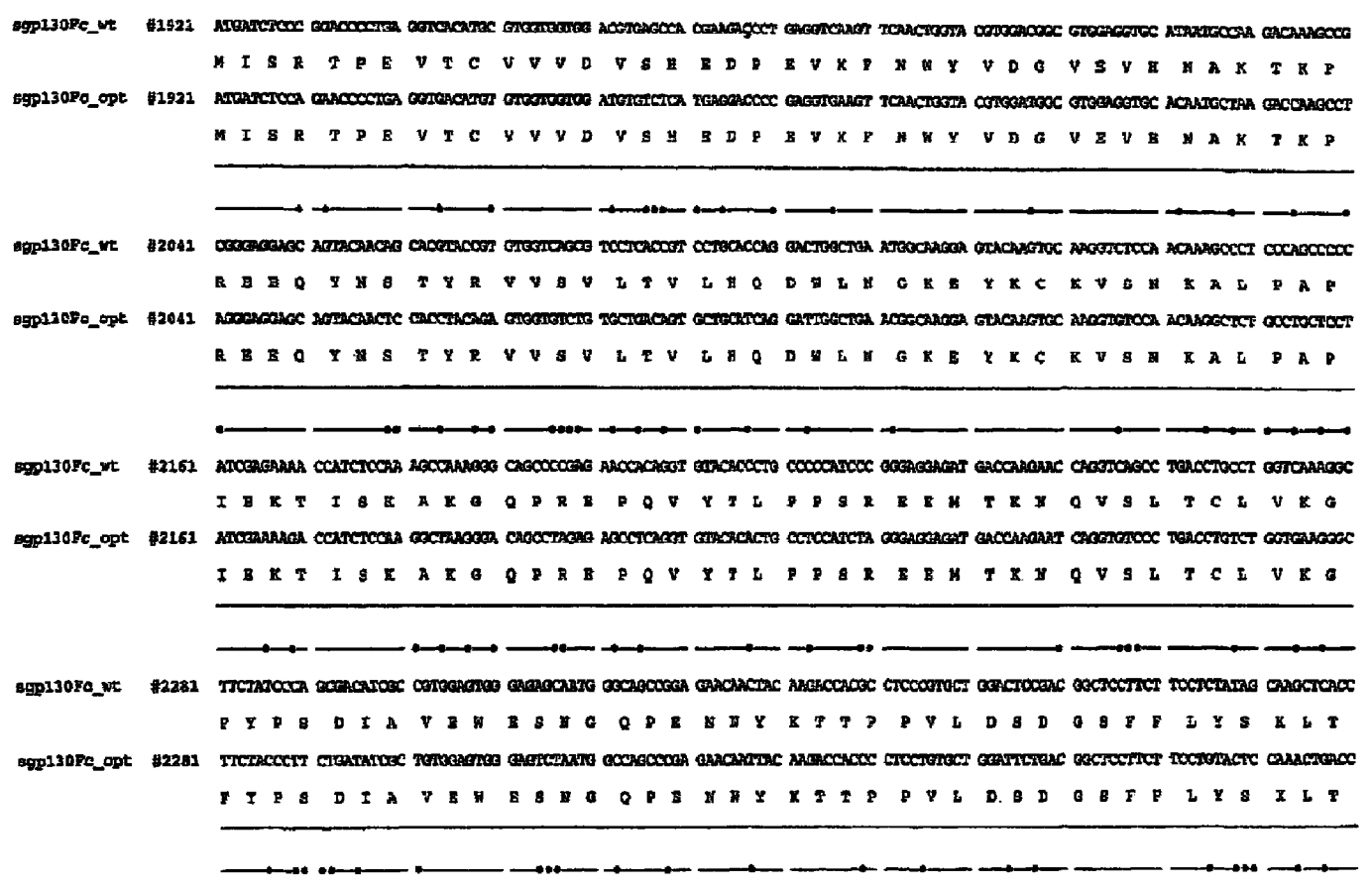

FIGS. 3A, 3B, 3C, 3D, 3E and 3F: sgp130(Fc) (Nucleotide Sequence and Amino Acid Sequence) for Expression in Mammalian Cells An alignment of the nucleotide sequence (SEQ ID NO: 12) with optimized codons (sgp130Fc_opt) vs. the original sequence (SEQ ID NO: 10) (sgp130Fc_wt) is shown. Amino acid sequences disclosed as SEQ ID NOS 11 and 13, respectively, in order of appearance.

Figure 4:
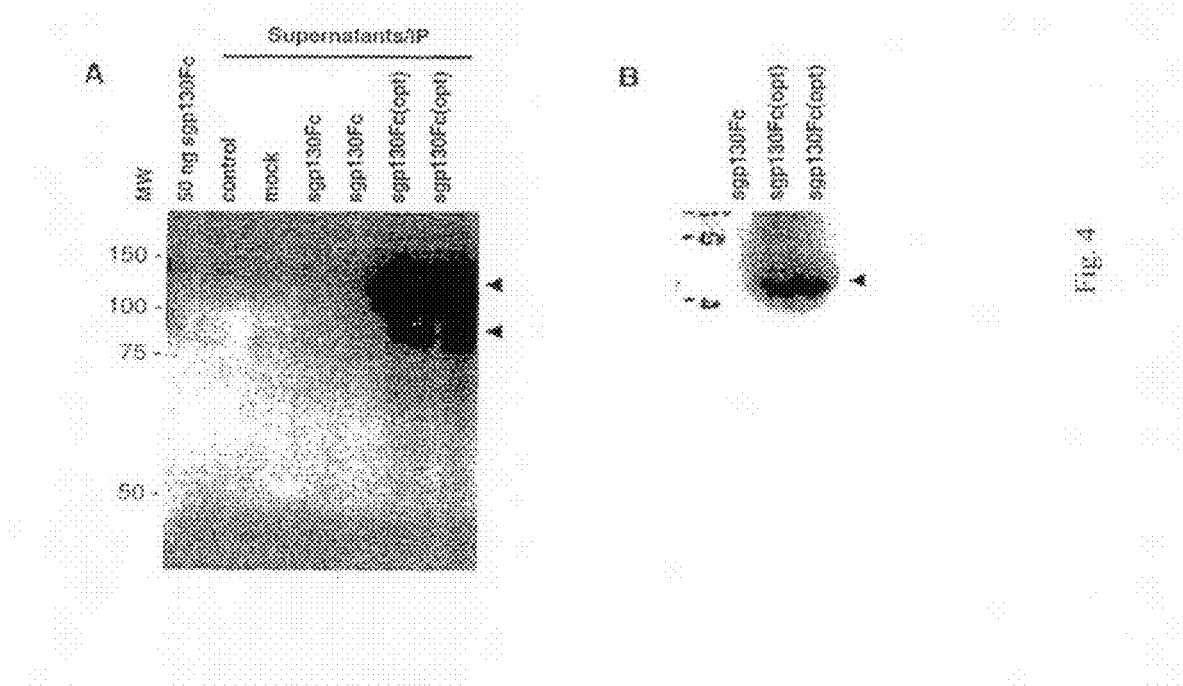

FIG. 4: Detection of sgp130Fc after Transient Transfection of HEK293 cells (A) or CHO Cells (B) with Wildtype or Optimized (opt) sgp130Fc Expression Plasmids The position of sgp130Fc is indicated by arrows (◄). Wildtype and optimized sgp130Fc expression was detected in two independent transfection experiments each. The different sizes of the protein (left panel) result from the leader sequence which has been partially cleaved off after secretion into the medium. The right panel represents the results derived from whole cell extracts from CHO cells (sgp130Fc with leader sequence).

FIG. 5: Detection of RNA Transcribed from Transfected Plasmid DNA (sgp130Fc; Neomycin Resistance Gene (NeoR)) by Gene-Specific RT-PCR HEK293 cells were transfected with an expression plasmid encoding either wildtype or optimized sgp130Fc. Transfection of the empty vector (mock) or non-transfected cells (control) served as negative controls. β-actin was amplified from total RNA to demonstrate the use of equal amounts of RNA in each single experiment.

FIG. 6: Expression of sgp130(D1-D3) in BL21(DE3)pLys Bacteria

The cDNA encoding sgp130(D1-D3) was cloned into the expression plasmid pET22b (Invitrogen, Carlsbad, Calif., USA) which in addition encodes a leading pelB sequence and a C-terminal His-tag. sgp130(D1-D3) was detected by western blot with a His-specific antibody and marked with an arrow (◄).

FIG. 7: Comparison and selection of different optimized sgp130Fc sequences.

The wt cDNA encoding sgp130Fc was optimized using different optimization algorithms ("Java Codon Adoption Tool" (JCat, and "UpGene" Gao et al. (2004), Biotechnol. Proc. 20(2): 443-8) and the resulting expression constructs were transfected into HEK293 cells. The expression of sgp130Fc was determined on RNA level by RT-PCR and on protein level by western blot as described earlier. The figure represents an example of the comparison of two different optimized sgp130Fc sequences (Opt1 and Opt2) with a sgp130Fc sequence optimized according to the present invention (Opt CONARIS).

Figure 8A:
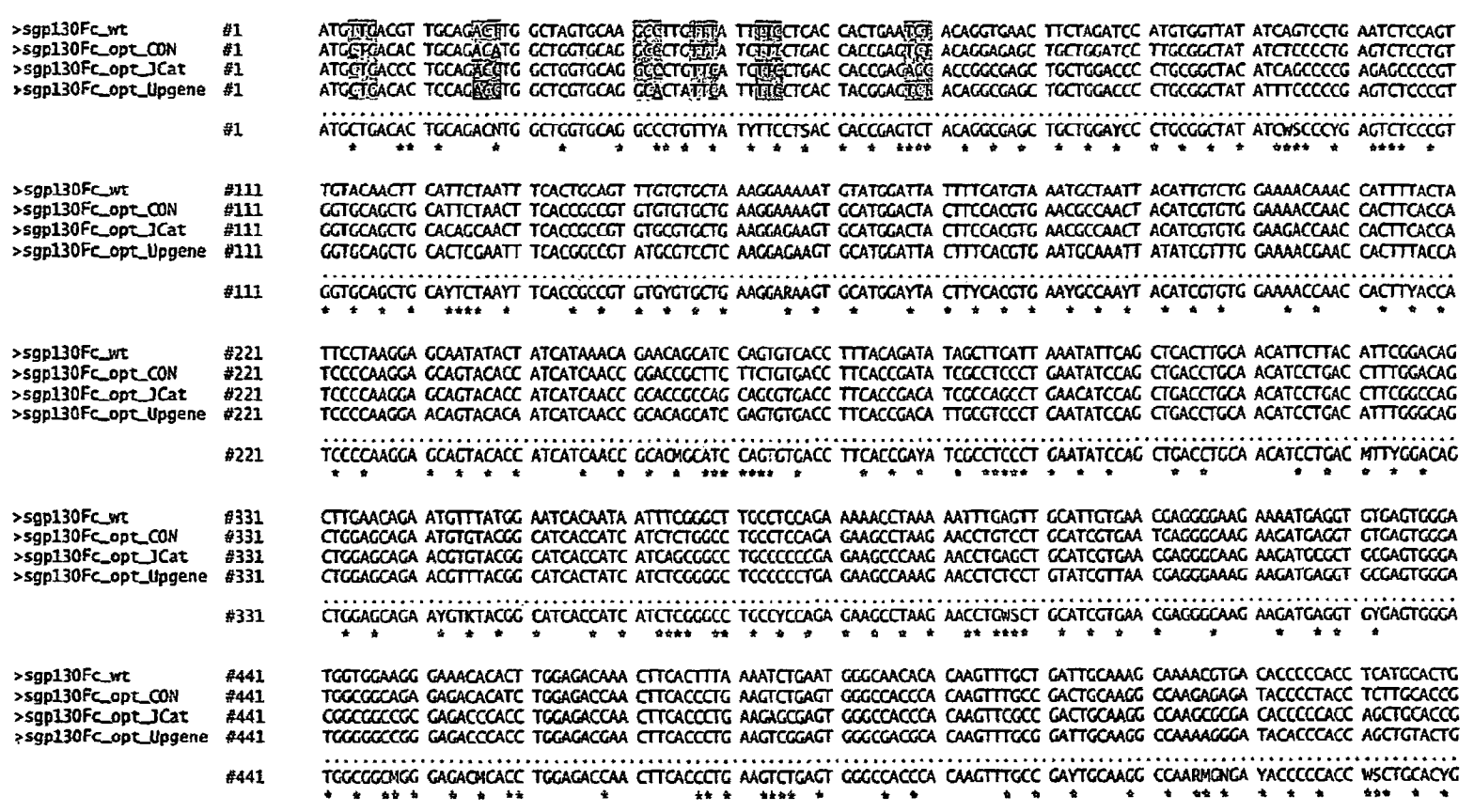
Figure 8B:
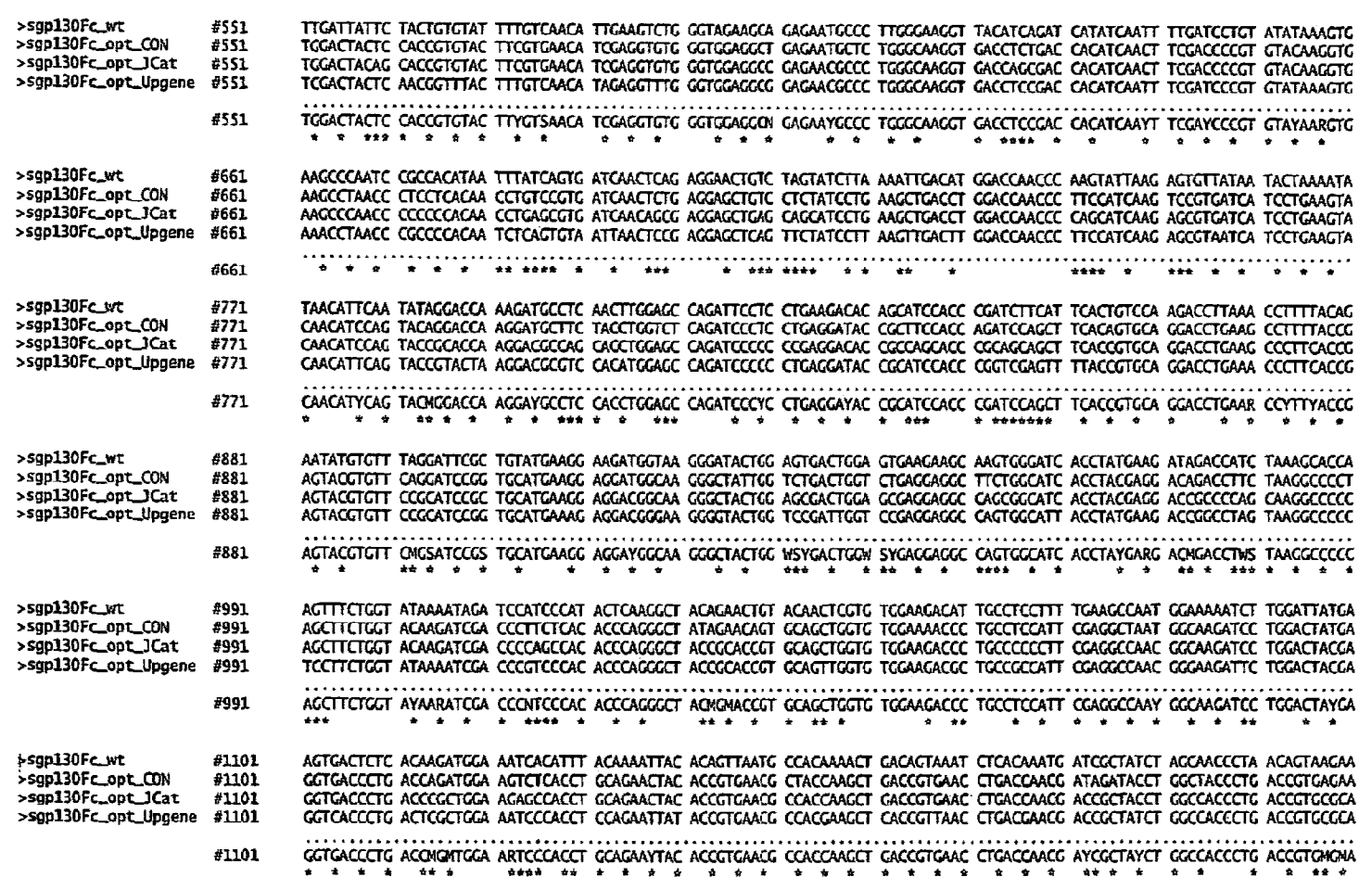
Figure 8C:
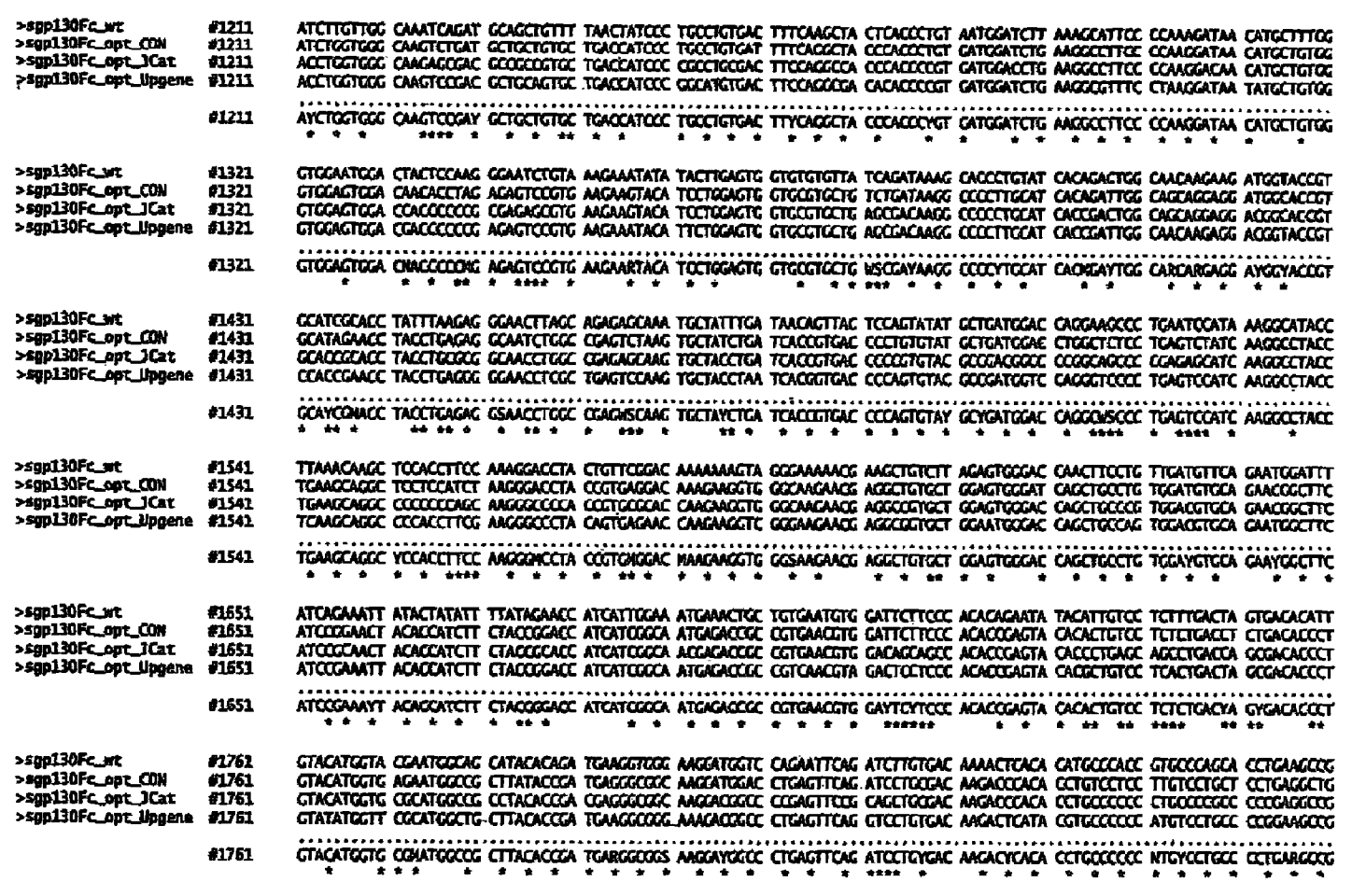
Figure 8D:
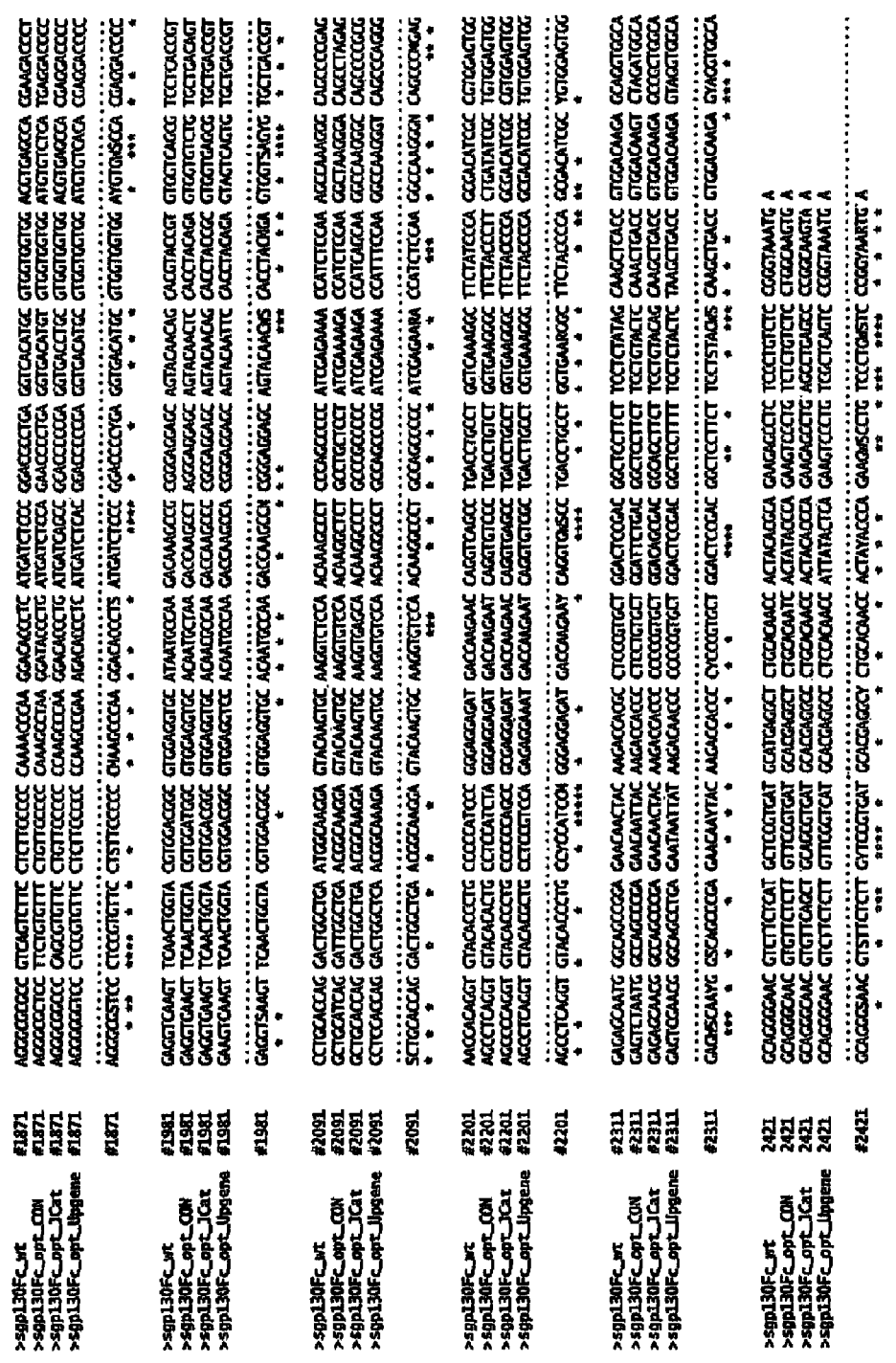

FIGS. 8A, 8B, 8C and 8D: Alignment of Different Optimized sgp130Fc cDNA Sequences and Comparison with the Unmodified Wild Type (wt) Sequence The shaded regions are showing a few examples of codons which either have been left unmodified (grey) as compared to the wild type (wt) or have been changed (partly in different ways) by the algorithms. Sequences disclosed as SEQ ID NOS 10 and 14-16, respectively, in order of appearance.

FIG. 9: The Table Indicates the Numbers of Base Pairs which are Different Between Two Compared Sequences sgp130Fc sequence optimized according to the present invention (opt_CON), JCat (opt_JCat) or UpGene (opt_Upgene).

Thus, the present invention relates to a nucleic acid molecule encoding sgp130 comprising the nucleic acid sequence (a) as depicted in FIGS. 2A, 2B and 2C (sgp130(D1-3)_opt) or FIGS. 3A, 3B, 3C, 3D, 3E and 3F (sgp130Fc_opt) or (b) a fragment or analogue thereof which maintains the codon usage pattern thereof.

The letter "s" of sgp130 means "soluble". The term "soluble" as used herein refers to a gp130 molecule lacking the intracellular domain and the transmembrane domain. The domains utilized in sgp130(D1-D3)_opt consist of the first three extracellular domains D1-D3 of gp130.

The term "fragment" as used herein refers to sgp130 fragments which comprise the entire or smaller parts of the optimized cDNA encoding the extracellular domain of gp130. Preferably, such fragments show a biological activity of the full length molecule, e.g. maintain the ability to inhibit the activity of the agonistic complex IL-6/sIL-6R. For the expression in bacteria such fragment also comprises sgp130 without the eukaryotic secretory leader sequence (MLTLQTWV-VQALFIFLTTESTG (SEQ ID NO: 1), Pos. 1 to 22). Moreover, a prokaryotic secretory leader sequence, e.g. pelB or OmpA could be cloned in front of the sgp130 sequence or parts of it and could be derived from the respective suitable expression plasmid, e.g. pET22b (Merck Biosciences GmbH, Bad Soden, Germany), pASK-IBA2, pASK-IBA12 (IBA, Goettingen, Germany). In addition the sgp130 protein can be expressed with or without Tag for purification purposes, e.g. $His_6$ (SEQ ID NO: 17), Strep, Myc or others.

The term "analogue" as used herein refers to a nucleic acid molecule which encodes the same amino acid sequence but which, through the redundancy of the genetic code, has a different nucleotide sequence. The term "codon usage pattern" as used herein refers to the average frequencies in the nucleotide sequence, e.g., highly expressed mammalian genes. Codon usage patterns for mammals, including humans can be found in the literature; see, e.g., Nakamura et al., Nucleic Acids Research 1996, 24:214-5. In the nucleic acid molecules of the present invention, the codon usage pattern is altered to more closely represent the codon bias of the host organism, e.g. a mammalian cell.

Alternatively, the present invention relates to a nucleic acid molecule, wherein at least 80%, preferably at least 90%, more preferably at least 95% and, most preferably at least 98% of the codons altered in the nucleic acid sequence of FIGS. 2A, 2B and 2C or 3A, 3B, 3C, 3D, 3E and 3F vs. the wild type sequence are present.

In a preferred embodiment, the nucleic acid molecule of the present invention is a DNA molecule.

The present invention includes expression vectors that comprise the nucleic acid molecules of the invention. The expression vectors can be constructed according to methods well known to the person skilled in the art; see, e.g., Sambrook, Molecular Cloning A Laboratory Manual, Cold Spring Harbor Laboratory (1989) N.Y. The "control elements" or "regulatory sequences" used for recombinant expression are those non-translated regions of the vector-enhancers, promoters, 5' and 3' untranslated regions which interact with host cellular proteins to carry out transcription and translation. Such elements may vary in their strength and specificity. Depending on the vector system and host utilised, any number of suitable transcription and translation elements, including constitutive and inducible promoters, may be used. In mammalian cell systems, promoters from mammalian genes or from mammalian viruses are preferable. Promoters and other expression regulation signals may be selected to be compatible with the host cell for which expression is designed. For example, mammalian promoters include the metallothionein promoter, which can be induced in response to heavy metals such as cadmium, and the β-actin 30 promoter. Viral promoters such as the SV40 large T antigen promoter, human cytomegalovirus (CMV) immediate early (IE) promoter, rous sarcoma virus LTR promoter, adenovirus promoter, or a HPV promoter, particularly the HPV upstream regulatory region (URR) may also be used. All these promoters are well described and readily available in the art.

In mammalian host cells, a number of viral-based expression systems may be utilised. In cases where an adenovirus is used as an expression vector, sequences encoding the polypeptide(s) of the present invention may be ligated into an adenovirus transcription/translation complex consisting of the late promoter and tripartite leader sequence. Insertion in a non-essential E1 or E3 region of the viral genome may be used to obtain a viable virus which is capable of expressing the antibody in infected host cells (Logan, J. and Shenk, T. (1984) Proc. Natl. Acad. Sci. 81:3655-3659). In addition, transcription enhancers, such as the Rous sarcoma virus (RSV) enhancer, may be used to increase expression in mammalian host cells.

Further examples of suitable viral vectors, include herpes simplex viral vectors, vaccinia or alpha-virus vectors and retroviruses, including lentiviruses and adeno-associated viruses. Gene transfer techniques using these viruses are known to those skilled in the art. Retrovirus vectors for example may be used to stably integrate the nucleic acid molecules of the invention into the host genome, although such recombination is not preferred. Replication-defective adenovirus vectors by contrast remain episomal and therefore allow transient expression. If it is necessary to generate a cell line that contains multiple copies of the sequence encoding the sgp130 polypeptides, vectors based on SV40 or EBV may be used with an appropriate selectable marker.

Human artificial chromosomes (HACs) may also be employed to deliver larger fragments of DNA than can be contained and expressed in a plasmid. HACs of 6 to 10 M are constructed and delivered via conventional delivery methods (liposomes, polycationic amino polymers, or vesicles) for therapeutic purposes.

Specific initiation signals may also be used to achieve more efficient translation. Such signals include the ATG initiation codon and adjacent sequences. In cases where sequences encoding the sgp130, its initiation codon, and upstream sequences are inserted into the appropriate expression vector, no additional transcriptional or translational control signals may be needed. However, in case where only a coding sequence for a fragment is inserted, exogenous translational control signals including the ATG initiation codon should be provided. Furthermore, the initiation codon should be in the correct reading frame to ensure translation of the entire insert.

Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125-162).

In addition, a host cell strain may be chosen for its ability to modulate the expression of the inserted sequences or to process the expressed polypeptide chains in the desired fashion. Post-translational processing which cleaves a "prepro" form of the polypeptide may also be used to facilitate correct insertion, folding and/or function. Different mammalian host cells which have specific cellular machinery and characteristic mechanisms for post-translational activities (e.g., CHO, HeLa, MDCK, HEK293, 293, COS-7 and W138), are available from the American Type Culture Collection (ATCC; Bethesda, Md.) and may be chosen to ensure the correct modification and processing of the foreign polypeptide chains.

For long-term, high-yield production of sgp130, stable expression in mammalian cells is preferred. For example, cell lines which stably express sgp130Fc may be transfected using expression vectors which may contain viral origins of replication and/or endogenous expression elements and one or more selectable marker genes on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

After the introduction of the recombinant vector(s), the host cells are grown in a selective medium, which selects for the growth of vector-containing cells. Any number of selection systems may be used to recover transformed cell lines. These include, but are not limited to, the herpes simplex virus thymidine kinase (Wigler, M. et al. (1977) Cell 11:223-32) and adenine phosphoribosyltransferase (Lowy, I. et al. (1980) Cell 22:817-23) genes which can be employed in tk.sup.– or aprt.sup.– cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567-70); npt, which confers resistance to the aminoglycosides neomycin and G-418 (Colbere-Garapin, F. et al (1981) J. Mol. Biol. 150:1-14) and als or pat, which confer resistance to chlorsulfuron and phosphinotricin acetyltransferase, respectively (Murry, supra). Additional selectable genes have been described, for example, trpB, which allows cells to utilise indole in place of tryptophan, or hisD, which allows cells to utilise histinol in place of histidine (Hartman, S. C. and R. C. Mulligan (1988) Proc. Natl. Acad. Sci. 85:8047-51). Recently, the use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121-131).

The person skilled also knows vectors and host cells for bacterial expression, e.g. bacteriophage, plasmid, or cosmid DNA expression vectors. Vectors suitable for use in the present invention include, but are not limited to the pSKK expression vector for expression in bacteria. Depending on the vector system and host utilised, any number of suitable transcription and translation elements, including constitutive and inducible promoters, may be used. For example, when cloning in bacterial systems, inducible promoters such as the hybrid lacZ promoter of the Bluescript™ phagemid (Stratagene, LaJolla, Calif.) or pSport1™ plasmid (Gibco BRL) and the like may be used.

Purification of the recombinant sgp130 is carried out by any one of the methods known for this purpose, i.e., any conventional procedure involving extraction, precipitation, chromatography, electrophoresis, or the like. A further purification procedure that may be used is affinity chromatography using monoclonal antibodies which bind the target polypeptide or a Tag fused to it, e.g., His, Strep or Myc, and which are produced and immobilized on a gel matrix contained within a column. Impure preparations containing the recombinant sgp130 are passed through the column. The sgp130 will be bound to the column by the specific antibody while the impurities will pass through. After washing the polypeptide is eluted from the gel by a change in pH or ionic strength and can then, if desired, dimerized and/or PEGylated.

Accordingly, the present invention also relates to a method of producing the sgp130 of the present invention, comprising culturing a host cell transformed with a nucleic acid molecule of the invention and recovering the sgp130 polypeptide from said host cell or the culture.

The sgp130 polypeptide produced from a nucleic acid molecule of the present invention is useful in the treatment and/or prevention of all the pathologies, in which the activity of the agonistic complex IL-6/sIL6R must be inhibited, e.g., for the treatment/prevention of bone resorption, hypercalcemia, cachexia, tumours, autoimmune diseases such as Crohn's disease and bacterial or viral infections.

The below examples explain the invention in more detail.

EXAMPLE 1

Material and Methods (A) Construct and Transfection

Figure 1:
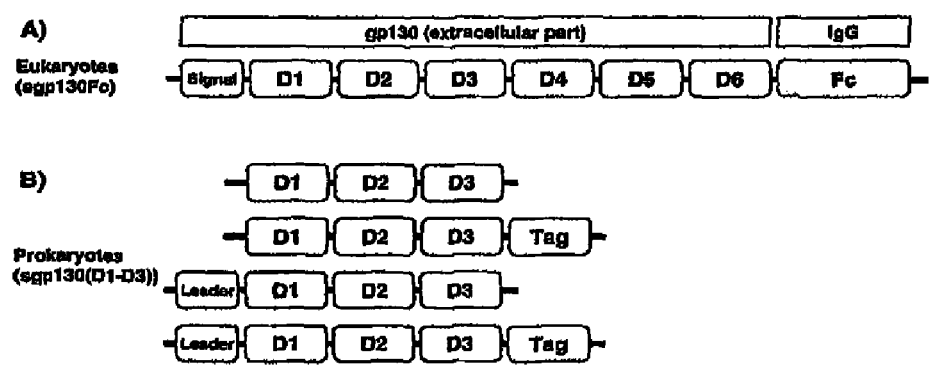
FIG. 1: Schematic Presentation of the Constructs

The cDNA encoding either wildtype or optimized sgp130Fc was cloned into the expression plasmid pDEST40 (Invitrogen, Carlsbad, Calif., USA) according to standard procedures. The wildtype sequence was derived from an expression plasmid which has been described in Jostock et al., Eur. J. Biochem. 268 (2001), 160-7 (FIG. 1; upper panel). The construct was sequence verified. $3 \times 10^5$ HEK293 cells were transiently transfected with 1 μg of plasmid and 3 μl of Fugene (Roche Diagnostics, Mannheim, Germany) in 3 ml of medium according to the manufacturer's manual. The cells were subsequently incubated for 24 h at 37° C. and supernatants and cells were harvested for further preparations of either total proteins or RNA, respectively.

One set of cells was transfected with the empty vector (mock), another set of cells was left untransfected (control). Both sets served as negative controls.

(B) Protein Extraction and Western Blot

The sgp130Fc protein was precipitated from the cell supernatants by adding 20 μl of Protein-A/G-Plus Agarose (Santa Cruz, Calif., USA). The slurry was incubated overnight at 4° C. and finally centrifuged. Bound proteins were extracted by boiling the agarose pellet in SDS sample buffer for 5 minutes at 100° C. In parallel the cells were scraped from the plates using a rubber policeman, harvested in 100 μl of PBS and centrifuged. All protein samples were separated on a standard acrylamide gel, transferred to a PDVF-membrane by semidry blotting and stained with a gp130-specific antibody (Hölzel Diagnostika, Köln, Germany). 50 ng of recombinant sgp130 served as positive control (sgp130).

(C) RNA Extraction

Total RNA was extracted from the cell pellets using a RNeasy Mini kit (Qiagen) according to the manufacturer's instructions. The following primers were used to determine RNA transcribed from the transfected plasmid DNA by RT-PCR: sgp130Fc_f: 5'-ATGAGGTGTGAGTGGGATGG-3' (SEQ ID NO: 2); sgp130Fc_r: 5'-ACCTTGCACTTG-TACTCCTTGC-3' (SEQ ID NO: 3); neomycin resistance gene NeoR_s: 5'-GATGCCTGCTTGCCGAATATC-3' (SEQ ID NO: 4); NeoR_r: 5'-CGCCAAGCTCTTCAGCAATATC-3' (SEQ ID NO: 5). Total RNA was initially reverse transcribed and the cDNA was amplified by 30 cycles of 30 seconds at 95° C. followed by 2 minutes at 57° C. and a final elongation step of 5 minutes at 72° C. Expected amplicon sizes: gp130: 1.712 bp, NeoR: 133 bp. The amplification of NeoR was performed to document an equal transfection efficiency of the plasmid. In addition, β-actin was amplified to demonstrated the use of equal amounts of total RNA in each experiment.

EXAMPLE 2

Highly Efficient Recombinant Production of sgp130Fc in HEK293 Cells

FIG. 4 demonstrates that in comparison to the wildtype expression plasmid the production of sgp130Fc was increased at least 10 to 20-fold in HEK293 cells transfected with the optimized sgp130Fc expression plasmid. On the RNA level (FIG. 5) a similar increase of sgp130Fc expression was detected with the optimized construct. This elevation of sgp130Fc RNA amounts was not due to a different transfection efficiency as shown by equal amounts of RNA encoded by the neomycin resistance gene which was also located on the expression plasmid.

The results indicate that the significant increase of sgp130Fc production after optimization of the cDNA sequence is partially based on an improved codon usage during translation but is mainly derived from the elevation of the corresponding RNA levels. This might be due to a more efficient transcription or a higher stability of the RNA.

EXAMPLE 3

Highly Efficient Recombinant Production of sgp130(D1-D3) in Bacteria (A) Constructs and Transformation The cDNA encoding either wildtype or optimized sgp130 (D1-D3) was cloned into the prokaryotic expression plasmid pET22b (Merck Biosciences GmbH, Bad Soden, Germany) according to standard procedures. The D1-D3 fragment was amplified afore from the pSVL-sgp130Fc plasmid described in Jostock et al. 2001. The construct was sequence verified and transformed into BL21(DE3)pLys bacteria (Invitrogen, Carlsbad, Calif., USA).

(B) Protein Expression and Western Blot 10 ml of bacterial suspension were diluted at 1:100 with LB-medium and grown at 30° C. overnight until the $OD_{600\,nm}$ reached a value of 0.3 (250 rpm). Protein expression was induced by the addition of 0.3 mM of IPTG (Isopropyl-beta-D-thiogalactopyranoside) (Qiagen, Hilden, Germany) and further incubation of the cells overnight at 25° C. The cells were pelleted by centrifugation at 4° C. and 4600 rpm for 30 minutes and the pellet was resuspended in 1 ml PBS (PAA Laboratories GmbH, Cölbe, Germany). Disruption of the cells was performed by sonication (3×30 sec, 10% cycle, 200% power) with a Bandelin Sonoplus HD 2070 sonicator. Insoluble material was pelleted at 13.000 rpm and 4° C. for 30 min and the pellet was resuspended in 1 ml of urea buffer (50 mM $NaH_2PO_4$, 8 M urea, pH8). An aliquot was diluted at 1:100 and subsequently analyzed by SDS PAGE according to standard protocols. His-tagged target proteins were detected with an anti-PentaHis antibody (Qiagen, Hilden, Germany).

(C) Results

Whereas the wildtype sequence generated a second shorter form of sgp130(D1-D3) (FIG. 6, left lane) this by-product was not observed with the optimized cDNA (FIG. 6, right lane). This unwanted variation of sgp130(D1-D3) is generated by further alternative transcriptional and translational start sides which have been eliminated by codon modifications in the optimized cDNA sequence. Subsequently the efficiency to produce the desired protein with the right size was increased at least at a factor of 3-fold.

EXAMPLE 4

Identification of the Best Optimized sgp130Fc cDNA Sequence

The wt sgp130Fc sequence was optimized using different optimization algorithms. The resulting sequences were synthesized, cloned into respective expression vectors and transfected into certain expression cells. The best sgp130Fc sequence was identified by detection of sgp130Fc expression on the RNA and the protein level. FIG. 7 shows an example of these sets of experiments and demonstrates that although three different optimized sequences were used only one sequence (namely "Opt CONARIS"), i.e., a sequence optimized according to the present invention, significantly increased the expression of sgp130Fc protein by HEK293 cells. FIGS. 8A, 8B, 8C and 8D represent an alignment of the same sequences. Although in all cases the optimization approach was based on an optimal codon usage in eukaryotes, the figure clearly demonstrates that the prediction for the optimal codon at a certain position is often completely different. FIG. 9 summarizes the findings of these alignments by showing the number of different base pairs between each of the sequences.

These results clearly demonstrate that the computer aided prediction of cDNA sequences for optimal protein expression in a certain organism has only an extremely limited value. The development of best optimized sequences makes it necessary to choose individual research approaches and must be accompanied by high innovative technologies and inventive power.

The invention claimed is:

1. An isolated nucleic acid molecule encoding sgp130 protein wherein the nucleic acid molecule comprises (a) the nucleic acid sequence of SEQ ID NO: 12 or (b) a fragment of (a) encoding a polypeptide that comprises extracellular domains D1 to D3 of sgp130, wherein the encoded polypeptide inhibits the activity of the agonistic complex IL-6/sIL-6R.

2. An isolated nucleic acid molecule which differs from (a) the nucleic acid sequence of SEQ ID NO: 12 or a fragment of SEQ ID NO: 12 that encodes a polypeptide comprising extracellular domain D1 to D3 of sgp130, in that at least 80% of the codons which are optimized in the nucleic acid sequence of SEQ ID NO: 12 or said fragment of SEQ ID NO: 12 as compared to the corresponding codons in wild type sgp130Fc nucleic acid sequence are present, wherein the encoded polypeptide of the nucleic acid sequence of SEQ ID NO: 12 or said fragment of SEQ ID NO: 12 inhibits the activity of the agonistic complex IL-6/sIL-6R.

3. The isolated nucleic acid molecule of claim 1 or 2 which is a DNA molecule.

4. An isolated expression vector containing a nucleic acid molecule of claim 1 or 2.

5. An isolated host cell containing an expression vector of claim 4.

6. The isolated host cell of claim 5 which is a mammalian host cell.

7. The isolated host cell of claim 6 which is a CHO or HEK293 cell.

8. A method of producing a sgp130 polypeptide comprising culturing the isolated host cell of claim 6 and recovering the polypeptide from said host cell or the culture.

9. A method of producing a sgp130 polypeptide comprising culturing the isolated host cell of claim 7 and recovering the polypeptide from said host cell or the culture.

* * * * *